(12) United States Patent
Yamada et al.

(10) Patent No.: US 12,070,188 B2
(45) Date of Patent: *Aug. 27, 2024

(54) ENDOSCOPE TIP COVER AND ENDOSCOPE

(71) Applicant: SHARP KABUSHIKI KAISHA, Sakai (JP)

(72) Inventors: Miho Yamada, Sakai (JP); Kiyoshi Minoura, Sakai (JP); Tokio Taguchi, Sakai (JP); Yasuhiro Shibai, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 567 days.

This patent is subject to a terminal disclaimer.

(21) Appl. No.: 17/283,188

(22) PCT Filed: Oct. 1, 2019

(86) PCT No.: PCT/JP2019/038772
§ 371 (c)(1),
(2) Date: Apr. 6, 2021

(87) PCT Pub. No.: WO2020/075579
PCT Pub. Date: Apr. 16, 2020

(65) Prior Publication Data
US 2021/0345860 A1 Nov. 11, 2021

(30) Foreign Application Priority Data
Oct. 10, 2018 (JP) .................. 2018-191660

(51) Int. Cl.
*A61B 1/00* (2006.01)
(52) U.S. Cl.
CPC ............................ *A61B 1/00137* (2013.01)

(58) Field of Classification Search
CPC ............ A61B 1/00101; A61B 1/00137; A61B 1/00089; A61B 1/00096; A61B 1/127;
(Continued)

(56) References Cited

U.S. PATENT DOCUMENTS

| 4,569,334 A | 2/1986 | Ohshiro |
| 6,530,881 B1 | 3/2003 | Ailinger et al. |

(Continued)

FOREIGN PATENT DOCUMENTS

| JP | 2004-041458 A | 2/2004 |
| JP | 4265729 B2 | 5/2009 |

(Continued)

OTHER PUBLICATIONS

Co-pending letter regarding a related co-pending U.S. Appl. No. 17/042,876, filed Sep. 28, 2020.
(Continued)

*Primary Examiner* — John P Leubecker
*Assistant Examiner* — Jae Woo
(74) *Attorney, Agent, or Firm* — ScienBiziP, P.C.

(57) ABSTRACT

An endoscope distal end cover (10) is a cover for protecting a distal end (20t) of an endoscope (20) which has an observation window at the distal end, including: a synthetic polymer film (13) which is to be located over the observation window (32) when the endoscope distal end cover is attached to the distal end of the endoscope, wherein the synthetic polymer film has a surface which includes a plurality of raised portions, when viewed in a normal direction of the synthetic polymer film, a two-dimensional size of the plurality of raised portions is in the range of more than 20 nm and less than 500 nm, and a static contact angle of water with respect to the surface is not less than 98°.

12 Claims, 7 Drawing Sheets

(58) Field of Classification Search
CPC ..... A61B 1/00071; A61B 1/0011; G02B 1/10; G02B 23/2476; G02B 23/2423; G02B 1/11; G02B 27/0006; G02B 1/18; C09D 5/006; C09D 5/1681; C09D 5/1662; B32B 27/18; B32B 27/08; B32B 27/30; B32B 3/30; C08F 290/06

See application file for complete search history.

(56) References Cited

U.S. PATENT DOCUMENTS

| | | |
|---|---|---|
| 9,826,890 B2 | 11/2017 | Osada et al. |
| 2003/0205475 A1 | 11/2003 | Sawitowski |
| 2005/0157981 A1 | 7/2005 | Berier et al. |
| 2007/0159698 A1 | 7/2007 | Taguchi et al. |
| 2008/0228035 A1* | 9/2008 | Hagihara ............... A61B 1/127 600/176 |
| 2012/0178995 A1 | 7/2012 | Newton, IV |
| 2012/0318772 A1 | 12/2012 | Minoura et al. |
| 2015/0140154 A1 | 5/2015 | Isurugi et al. |
| 2015/0196194 A1 | 7/2015 | Wu et al. |
| 2015/0259316 A1 | 9/2015 | Morone et al. |
| 2016/0113274 A1* | 4/2016 | Yamada ................... A61L 9/00 422/4 |
| 2017/0066207 A1* | 3/2017 | Hayashi .............. C08F 290/067 |
| 2017/0320281 A1 | 11/2017 | Hayashi et al. |
| 2019/0001612 A1 | 1/2019 | Hayashi et al. |
| 2019/0016900 A1 | 1/2019 | Hayashi et al. |
| 2019/0077130 A1 | 3/2019 | Shibai et al. |
| 2019/0136070 A1* | 5/2019 | Aizenberg ........... A61B 1/0125 |
| 2019/0276577 A1 | 9/2019 | Shibai et al. |

FOREIGN PATENT DOCUMENTS

| | | |
|---|---|---|
| JP | 2009-166502 A | 7/2009 |
| JP | 2014-097093 A | 5/2014 |
| JP | 2014-200974 A | 10/2014 |
| JP | 6066390 B1 | 1/2017 |
| JP | 2019-051638 A | 4/2019 |
| JP | 2019-156879 A | 9/2019 |
| WO | 2011/125486 A1 | 10/2011 |
| WO | 2013/183576 A1 | 12/2013 |
| WO | 2015/163018 A1 | 10/2015 |
| WO | 2016/174893 A1 | 11/2016 |
| WO | 2018/012340 A1 | 1/2018 |
| WO | 2018/012342 A1 | 1/2018 |

OTHER PUBLICATIONS

Non-Final Office Action issued on Dec. 18, 2023 for U.S. Appl. No. 17/042,876.

Non-Final Rejection dated Aug. 2, 2023 for U.S. Appl. No. 17/042,876.

Maruyasu Corporation, ("What are the characteristics of polyurethane, a stretch material you should know", https://www.maruyasu-fil.com/knit-magazine/2220 Oct. 11, 2016 (2016)—"Maruyasu") (Year: 2016).

Methyl methacrylate, Wikipedia, https://web.archive.org/web/20160412044009/https://en .wikipedia.org/wiki/Poly(methyl_methacrylate), Apr. 12, 2016 (2016)—"Methyl methacrylate") (Year: 2016).

1 Final Office Action issued on Apr. 8, 2024 for U.S. Appl. No. 17/042,876.

\* cited by examiner (a)

(b)

(a)

(b)

(a)

(b)

(c)

(a)

(b)

(c)

(a)

(b)

(a)

(b)

(c)

ENDOSCOPE TIP COVER AND ENDOSCOPE

TECHNICAL FIELD

The present invention relates to an endoscope distal end cover for protecting the distal end of endoscopes (including rigid and flexible endoscopes), an endoscope including an endoscope distal end cover, and a method for using an endoscope distal end cover.

BACKGROUND ART

An antireflection technique which has been receiving attention in recent years is forming over a substrate surface a microscopic uneven pattern in which the interval of recessed portions or raised portions is not more than the wavelength of visible light ($\lambda$=380 nm to 780 nm). See Patent Document No. 1 and Patent Document No. 2. The two-dimensional size of a raised portion of an uneven pattern which performs an antireflection function is not less than 10 nm and less than 500 nm. Here, the "two-dimensional size" of the raised portions refers to the area equivalent circle diameter of the raised portions viewed in a direction normal to the surface. For example, when the raised portions have a conical shape, the two-dimensional size of the raised portions is equivalent to the diameter of the base of the cone. The same applies to the "two-dimensional size" of the recessed portions.

The present applicant conceived a method for producing an antireflection film (an antireflection surface) which has a moth-eye structure with the use of an anodized porous alumina layer. Using the anodized porous alumina layer enables manufacture of a mold which has an inverted moth-eye structure with high mass-productivity (see, for example, Patent Documents No. 1 through No. 4). The entire disclosures of Patent Documents No. 1 through No. 4 are incorporated by reference in this specification.

The present applicant developed the above-described technology and arrived at a synthetic polymer film whose surface has a microbicidal effect (see, for example, Patent Document No. 5). The entire disclosures of Patent Document No. 5 are incorporated by reference in this specification.

The present applicant discloses an optical film which has excellent antireflection properties and has excellent anti-smear properties and abrasion resistance in Patent Document No. 6, and films which have excellent anti-smear properties in Patent Documents No. 7 and No. 8. The entire disclosures of Patent Documents No. 6 through No. 8 are incorporated by reference in this specification.

However, when blood or body fluid is adhered to an observation window of an endoscope, disadvantageously, the field of view for observation cannot be maintained. Endoscopes presently used include, for example, a mechanism for washing the observation window. Washing of the observation window is realized by washing away the blood or the like adhered to the observation window with a washer liquid ejected from a nozzle provided at the distal end of the endoscope. The washer liquid adhered to the observation window is removed by air blown out of the nozzle.

CITATION LIST

Patent Literature

Patent Document No. 1: Japanese Patent No. 4265729
Patent Document No. 2: Japanese Laid-Open Patent Publication No. 2009-166502
Patent Document No. 3: WO 2011/125486
Patent Document No. 4: WO 2013/183576
Patent Document No. 5: WO 2015/163018 (Japanese Patent No. 5788128)
Patent Document No. 6: WO 2016/174893 (Japanese Patent No. 5951165)
Patent Document No. 7: WO 2018/012340
Patent Document No. 8: WO 2018/012342

SUMMARY OF INVENTION

Technical Problem

However, even if an endoscope used has the above-described washing mechanism, washing the observation window takes time (washing cannot be completed within a short time). Further, washing sometimes causes blood (and a washer liquid contaminated with blood) to spread over the observation window so that observation can be difficult. When the observation window is not cleaned by washing, it is necessary to once pull the distal end of the endoscope out of a body cavity.

An object of the present invention is to provide an endoscope distal end cover and an endoscope in which adhesion of blood or body fluid to the observation window of the endoscope is suppressed and the observation window can be kept clean or easily washed as compared with the conventional systems.

Solution to Problem

According to an embodiment of the present invention, solutions described in the following Items are provided.

[Item 1]
An endoscope distal end cover for protecting a distal end of an endoscope which has an observation window at the distal end, comprising:
  a synthetic polymer film which is to be located over the observation window when the endoscope distal end cover is attached to the distal end of the endoscope,
  wherein the synthetic polymer film has a surface which includes a plurality of raised portions,
  when viewed in a normal direction of the synthetic polymer film, a two-dimensional size of the plurality of raised portions is in the range of more than 20 nm and less than 500 nm, and
  a static contact angle of water with respect to the surface is not less than 98°.

[Item 2]
The endoscope distal end cover of Item 1, wherein the static contact angle of water with respect to the surface of the synthetic polymer film is not less than 128°. The static contact angle of hexadecane with respect to the surface is preferably not less than 35°.

[Item 3]
The endoscope distal end cover of Item 1 or 2, further comprising a liquid film of a water-repellent oil covering a surface of at least a portion of the synthetic polymer film located on the observation window.

[Item 4]

The endoscope distal end cover of Item 3, wherein the water-repellent oil is a silicone oil or a fluoric oil.

[Item 5]

The endoscope distal end cover of Item 3 or 4, wherein the water-repellent oil is a silicone oil whose kinematic viscosity is lower than 350 mm$^2$/s.

[Item 6]

The endoscope distal end cover of Item 3 or 4, wherein the water-repellent oil is a silicone oil whose kinematic viscosity is equal to or lower than 10 mm$^2$/s.

[Item 7]

The endoscope distal end cover of any of Items 1 to 6, wherein the synthetic polymer film includes a resin film which is made of a photocurable resin.

[Item 8]

The endoscope distal end cover of Item 7, wherein the synthetic polymer film further includes a water-repellent and oil-repellent layer formed on the resin film.

[Item 9]

The endoscope distal end cover of Item 7 or 8, wherein the photocurable resin contains a first polymerizable fluoric compound which contains a fluorine element, the first polymerizable fluoric compound has a plurality of polymerizable functional groups and has a molecular weight of not less than 1000 and not more than 5000, and at the lapse of 5 minutes since placing a 200 μL drop of water on the surface of the synthetic polymer film, a pH of an aqueous solution is not less than 6.5 and not more than 7.5.

[Item 10]

The endoscope distal end cover of Item 9, wherein the photocurable resin contains a photopolymerization initiator, and the photopolymerization initiator contains at least one of the group consisting of ethanone,1-[9-ethyl-6-(2-methylbenzoyl)-9H-carbazole-3-yl]-,1-(C)-acetyloxime), 2-hydroxy-1-{4-[4-(2-hydroxy-2-methyl-propionyl)-benzyl]phenyl}-2-methyl-propan-1-one, and 1-[4-(2-hydroxyethoxy)-phenyl]-2-hydroxy-2-methyl-1-propane-1-one.

[Item 11]

The endoscope distal end cover of Item 9 or 10, wherein the photocurable resin further contains a second polymerizable fluoric compound which contains a fluorine element, and the second polymerizable fluoric compound is a monofunctional polymerizable compound and has a molecular weight of not less than 100 and not more than 1000.

[Item 12]

The endoscope distal end cover of any of Items 9 to 11, wherein a proportion of the first polymerizable fluoric compound to the photocurable resin is not less than 1 mass % and not more than 5 mass %.

[Item 13]

An endoscope comprising the endoscope distal end cover as set forth in any of Items 1 to 12, the endoscope distal end cover being attached to the endoscope.

Advantageous Effects of Invention

According to an embodiment of the present invention, an endoscope distal end cover, an endoscope and a method for using an endoscope distal end cover are provided in which adhesion of blood or body fluid to the observation window of the endoscope is suppressed and the observation window can be kept clean or easily washed as compared with the conventional systems.

DESCRIPTION OF EMBODIMENTS

Hereinafter, the configurations of an endoscope distal end cover, an endoscope, and a method for using an endoscope distal end cover according to an embodiment of the present invention are described with reference to the drawings. The endoscope distal end cover and the endoscope according to an embodiment of the present invention are not limited to those illustrated in the following paragraphs.

Figure 1:
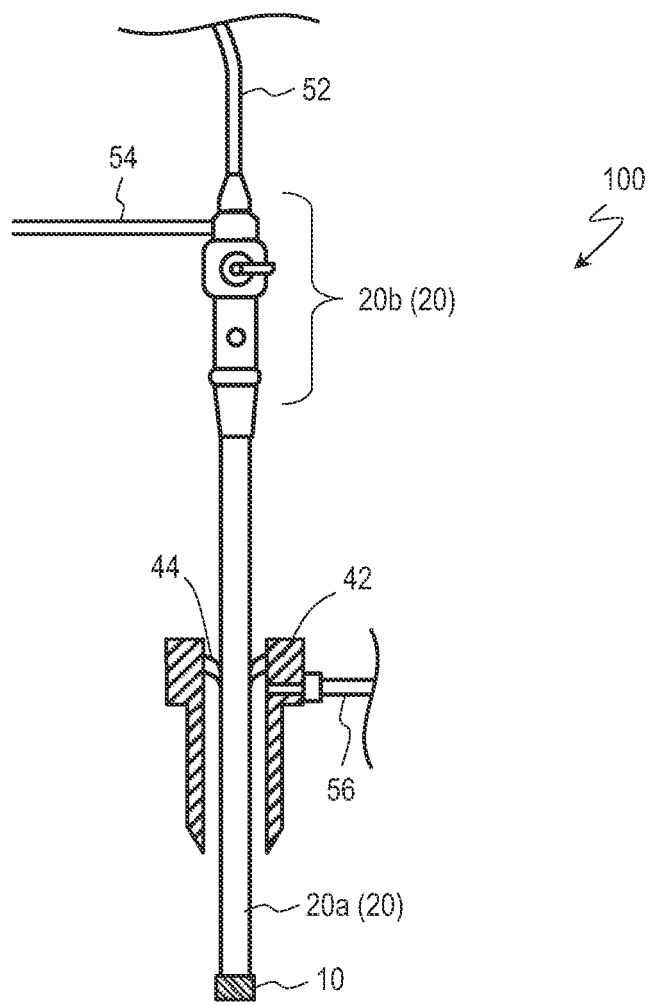
FIG. 1(a) is a schematic diagram of an endoscope system 100 which includes an endoscope 20 of an embodiment of the present invention.
FIG. 1(b) is a schematic diagram of an endoscope distal end cover 10 of an embodiment of the present invention.
Figure 1:
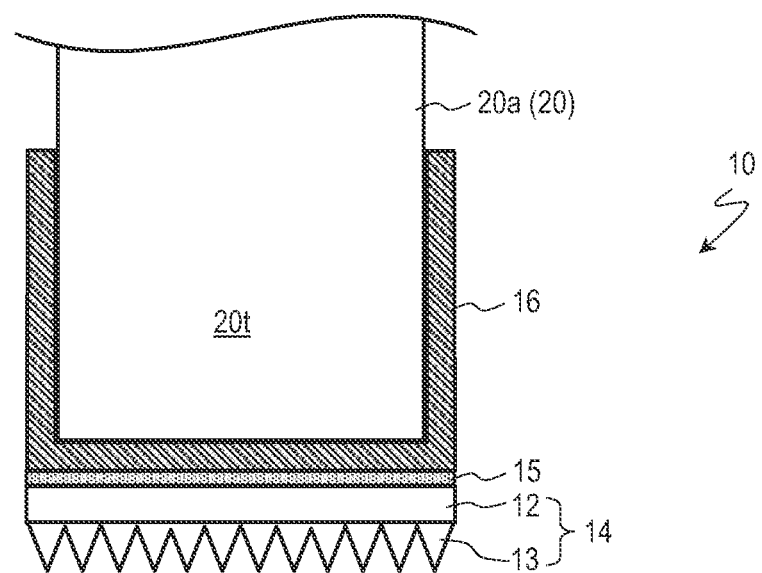

FIG. 1(a) is a schematic diagram of an endoscope system 100 which includes an endoscope 20 of an embodiment of the present invention. FIG. 1(b) is a schematic diagram of an endoscope distal end cover 10 of an embodiment of the present invention.

The endoscope 20 described herein is an endoscope for use in laparoscopic surgery, although the endoscope distal end cover of an embodiment of the present invention is not limited to illustrated endoscopes but widely applicable to endoscopes with an observation window at the distal end.

For example, after a trocar (insertion device) 42 is pierced into a body cavity from the abdominal surface of a patient, the insertion section 20a of the endoscope 20 is inserted into the body cavity through the trocar 42, and various treatments are performed while the inside of the body cavity is displayed on a monitor. The control section 20b of the endoscope 20 is connected to a computer and a light source unit via a universal cable and is capable of various operations, including illuminating, photographing, operation of a forceps (not shown), supply of a washer liquid or washer gas through a gas/liquid supply tube 54, etc. An insufflation gas (carbon dioxide gas) is supplied into an abdominal cavity through an insufflation tube 56 connected with the trocar 42. The trocar 42 has a valve 44. The valve 44 is to prevent the insufflation gas from leaking out of the opening of the trocar 42.

The end face of the endoscope distal end 20t includes, for example, an observation window 32, illumination windows 34a, 34b, a forceps opening 36 and an ejection nozzle as shown in FIG. 6(a). The observation window 32 is washed by ejecting a washer liquid and/or compressed air from the ejection nozzle 38 onto the observation window 32. However, as previously described, washing the observation window takes time (washing cannot be completed within a short time). Further, washing sometimes causes blood (and a washer liquid contaminated with blood) to spread over the observation window so that observation can be difficult. When the observation window is not cleaned by washing, it is necessary to once pull the distal end of the endoscope out of a body cavity.

When the endoscope distal end cover 10 of an embodiment of the present invention is attached to the endoscope distal end 20t, adhesion of blood or body fluid to the observation window 32 of the endoscope 20 is suppressed so that the observation window can be kept clean as compared with the conventional systems.

As shown in FIG. 1(b), the endoscope distal end cover 10 (hereinafter, also simply referred to as "cover") includes a synthetic polymer film 13 which is to be located over the observation window when the endoscope distal end cover 10 is attached to the endoscope distal end 20t. The synthetic polymer film 13 has a surface which includes a plurality of raised portions. When viewed in a normal direction of the synthetic polymer film 13, the two-dimensional size of the plurality of raised portions is in the range of more than 20 nm and less than 500 nm. The static contact angle of water with respect to the surface is not less than 150°. The static contact angle of hexadecane with respect to the surface is not less than 60°. That is, the synthetic polymer film 13 has a moth-eye structure over the surface and exhibits excellent water repellency and excellent oil repellency, so that adhesion of blood or body fluid can be suppressed. Even if there is blood or the like adhered to the surface of the synthetic polymer film 13, the surface can be cleaned more easily and more assuredly than the conventional systems. The moth-eye structure produces an antireflection function (for example, reflectance of 0.2% or less) and, therefore, a large amount of light can be guided to the observation window as compared with the conventional systems.

The cover 10 includes, for example, a synthetic polymer film 13, a base film 12 provided on the endoscope 20 side of the synthetic polymer film 13, and a cover member 16 provided on the endoscope 20 side of the base film 12 as shown in FIG. 1(b). The synthetic polymer film 13 is formed from, for example, a photocurable resin. The synthetic polymer film 13 and the base film 12 are provided only over the end face of the distal end 20t. The cover member 16 has greater tensile elongation than the base film 12 and is also provided on the lateral surface of the distal end 20t. The base film 12 and the synthetic polymer film 13 provided on the base film 12 constitute a film 14 which has a moth-eye structure over the surface.

The synthetic polymer film 13 that has the moth-eye structure at the surface is preferably formed from a photocurable resin as will be described later. Therefore, the synthetic polymer film 13 has relatively poor stretchability. As will be described later, in order to form the synthetic polymer film 13 according to a roll-to-roll method, using as the base film 12 a film which is relatively stiff, i.e., a film which has relatively high elastic modulus (e.g., PET, TAC, PC), is preferred. In such a case, it is difficult to directly cover the endoscope distal end 20t with the film 14 that has the moth-eye structure. Particularly, it is difficult to bring the film 14 into close contact with the end face such that no air gap is present between the film 14 and the observation window 32.

In view of the foregoing, the cover member 16 provided has greater tensile elongation than the base film 12, and the distal end 20t is covered with the cover member 16. The tensile elongation (elongation at break in tensile test: ASTM D638) of the cover member 16 is preferably not less than 100%, more preferably not less than 200%, still more preferably not less than 300%. The cover member 16 may be, for example, a film whose thickness is not more than 500 µm (see, for example, FIG. 3(a) and FIG. 3(b)). Alternatively, the cover member 16 may have the shape of a cap covering the endoscope distal end 20t (the shape of a hollow cylinder with one end being closed) (see FIG. 3(c)).

The cover member 16 and the film 14 (base film 12) are joined together by, for example, an adhesive layer 15. When the cover member 16 and the film 14 can be thermally welded together, the adhesive layer 15 may be omitted. As a matter of course, the cover member 16 preferably has high transmittance for visible light. The transmittance for visible light of the cover member 16 is preferably not less than 80%, more preferably not less than 90%.

Examples of the polymer material suitably used for the cover member 16 include acrylic elastomers, olefin elastomers, styrene elastomers, vinyl chloride elastomers, ester elastomers, fluoroelastomers, and silicone elastomers (silicone rubber). When a film is used as the cover member 16, not only the aforementioned elastomers but also acrylic resins, polyolefin resins, polystyrene resins, vinyl chloride resins, polyester resins, fluororesins and silicone resins, whose elongation is smaller than those of the elastomers, can also be used. When a thermally-shrinkable film is used among these resins, the cover member (cover film) 16 can be easily brought into close contact with the endoscope distal end 20t. Herein, "olefin" includes polyethylene, polypropylene, and copolymers of ethylene and α-olefin (propylene, butene, hexene, octene, 4-methylpentene, etc.).

The cover member 16 preferably has high transparency for visible light. The transparency for visible light is preferably not less than 80%, more preferably not less than 90%. From the viewpoint of transparency, acrylic, polypropylene, styrene, vinyl chloride and polyester materials are preferred.

The method of securing the cover member 16 to the endoscope distal end 20t after the cover member 16 is attached to the endoscope distal end 20t is not particularly limited. For example, the cover member 16 may be secured to the distal end 20t using a stretchable medical tape. Alternatively, an adhesive agent (including a pressure sensitive adhesive) may be used. Further, a securing member may be used which includes a cylindrical attaching member capable of pressing the cover member 16 against the lateral surface of the distal end 20t when the cover member 16 is attached to the endoscope distal end 20t (see, for example, FIG. 4(a), FIG. 4(b) and FIG. 4(c)). As a matter of course, a plurality of securing methods may be used in combination.

Next, the configuration of the synthetic polymer film 13 is described with reference to FIG. 2(a) and FIG. 2(b).

Figure 2:
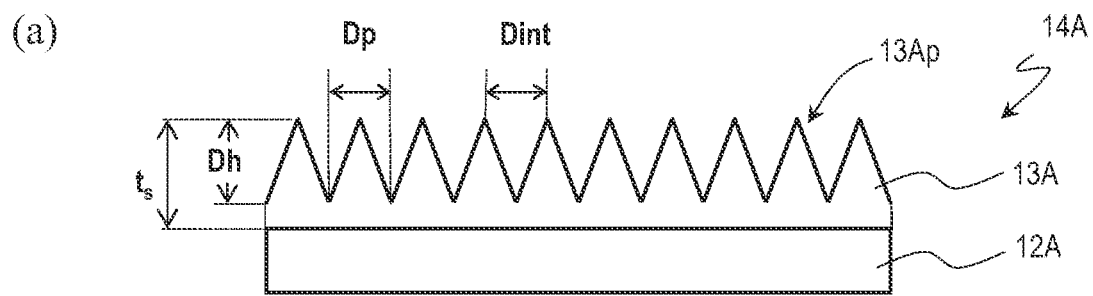
FIG. 2(a) and FIG. 2(b) are schematic cross-sectional views of synthetic polymer films 13A and 13B, respectively, which are suitably used in the endoscope distal end cover 10 of an embodiment of the present invention.
Figure 2:
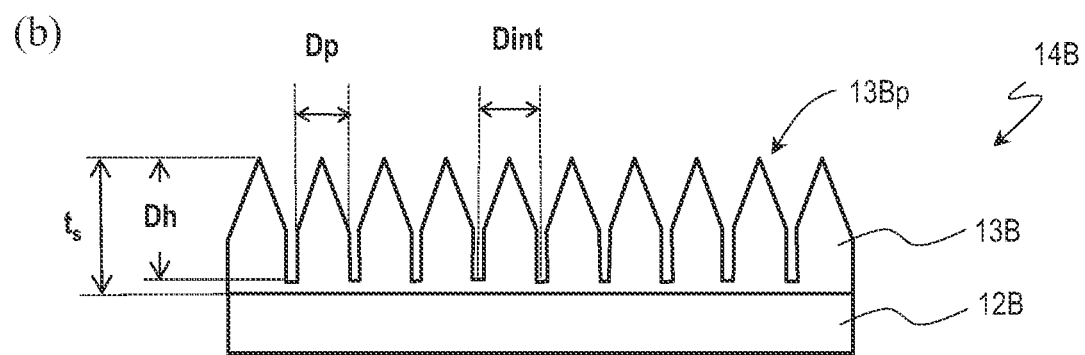

FIG. 2(a) and FIG. 2(b) are schematic cross-sectional views of synthetic polymer films 13A and 13B, respectively, which are suitably used in the endoscope distal end cover 10.

The synthetic polymer films 13A and 13B illustrated herein are provided on base films 12A and 12B, respectively.

A film 14A shown in FIG. 2(a) includes a base film 12A and a synthetic polymer film 13A provided on the base film 12A. The synthetic polymer film 13A has a plurality of raised portions 13Ap over its surface. The plurality of raised portions 13Ap constitute a moth-eye structure. When viewed in a normal direction of the synthetic polymer film 13A, the two-dimensional size of the raised portions 13Ap, $D_p$, is in the range of more than 20 nm and less than 500 nm. Here, the "two-dimensional size" of the raised portions 13Ap refers to the diameter of a circle equivalent to the area of the raised portions 13Ap when viewed in a normal direction of the surface. When the raised portions 13Ap have a conical shape, for example, the two-dimensional size of the raised portions 13Ap is equivalent to the diameter of the base of the cone. The typical adjoining distance of the raised portions 13Ap, $D_{int}$, is more than 20 nm and not more than 1000 nm. When the raised portions 13Ap are densely arranged so that there is no gap between adjoining raised portions 13Ap (e.g., the bases of the cones partially overlap each other) as shown in FIG. 2(a), the two-dimensional size of the raised portions 13Ap, $D_p$, is equal to the adjoining distance $D_{int}$. The typical height of the raised portions 13Ap, $D_h$, is not less than 50 nm and less than 500 nm. The height $D_h$ of the raised portions 13Ap may be not more than 150 nm. The thickness of the synthetic polymer film 13A, $t_s$, is not particularly limited but only needs to be greater than the height $D_h$ of the raised portions 13Ap.

The synthetic polymer film 13A shown in FIG. 2(a) has the same moth-eye structure as the antireflection films disclosed in Patent Documents No. 1 through No. 4. From the viewpoint of producing an antireflection function, it is preferred that the surface has no flat portion, and the raised portions 13Ap are densely arranged over the surface. Further, the raised portions 13Ap preferably has a such shape that the cross-sectional area (a cross section parallel to a plane which is orthogonal to an incoming light ray, e.g., a cross section parallel to the surface of the base film 12A) increases from the air side to the base film 12A side, e.g., a conical shape. From the viewpoint of suppressing interference of light, it is preferred that the raised portions 13Ap are arranged without regularity, preferably randomly. Furthermore, the uneven structure of the synthetic polymer film 13A produces a so-called Lotus effect and therefore exhibits excellent water repellency and excellent oil repellency.

A film 14B shown in FIG. 2(b) includes a base film 12B and a synthetic polymer film 13B provided on the base film 12B. The synthetic polymer film 13B has a plurality of raised portions 13Bp over its surface. The plurality of raised portions 13Bp constitute a moth-eye structure. In the film 14B, the configuration of the raised portions 13Bp of the synthetic polymer film 13B is different from that of the raised portions 13Ap of the synthetic polymer film 13A of the film 14A. Descriptions of features which are common with those of the film 14A are sometimes omitted.

When viewed in a normal direction of the synthetic polymer film 13B, the two-dimensional size of the raised portions 13Bp, $D_p$, is in the range of more than 20 nm and less than 500 nm. The typical adjoining distance of the raised portions 13Bp, $D_{int}$, is more than 20 nm and not more than 1000 nm, and $D_p<D_{int}$ holds. That is, in the synthetic polymer film 13B, there is a flat portion between adjoining raised portions 13Bp. The raised portions 13Bp have the shape of a cylinder with a conical portion on the air side. The typical height of the raised portions 13Bp, $D_h$, is not less than 50 nm and less than 500 nm. The raised portions 13Bp may be arranged regularly or may be arranged irregularly. When the raised portions 13Bp are arranged regularly, $D_{int}$ also represents the period of the arrangement. This also applies to the synthetic polymer film 13A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 13Ap of the synthetic polymer film 13A shown in FIG. 2(a) but also surficial nanostructures that are formed by raised portions which have a part where the cross-sectional area (a cross section parallel to the film surface) is constant as do the raised portions 13Bp of the synthetic polymer film 13B shown in FIG. 2(b). Note that, however, the tip of the conical portion may be rounded.

As disclosed in Patent Document No. 5, the synthetic polymer film may further have a plurality of second raised portions which are superimposedly formed over a plurality of first raised portions. Herein, raised portions of the above-described synthetic polymer film which have a two-dimensional size in the range of more than 20 nm and less than 500 nm are referred to as "first raised portions". The two-dimensional size of the second raised portions is smaller than the two-dimensional size of the first raised portions and does not exceed 100 nm.

A mold for forming the moth-eye structure such as illustrated in FIG. 2(a) and FIG. 2(b) over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Patent Documents No. 2 through No. 5. That is, by alternately and repeatedly performing the anodization step and the etching step on an aluminum film deposited on a base or on an aluminum base through multiple cycles, a moth-eye mold is obtained which includes a porous alumina layer which has an inverted moth-eye structure.

The surface of the synthetic polymer film 13 has the moth-eye structure obtained by inverting the surficial nanostructure of the moth-eye mold. According to the surficial nanostructure of the moth-eye mold used, the synthetic polymer films 13A and 13B shown in FIG. 2(a) and FIG. 2(b), respectively, can be produced. The material that forms the synthetic polymer film 13 is not limited to the UV-curable resin but may be a photocurable resin which is curable by visible light.

[Synthetic Polymer Film]

Sample films which had the same configuration as the film 14A shown in FIG. 2(a) were produced using UV-curable resins of different compositions. The materials used in the UV-curable resins for production of the synthetic polymer films of respective sample films are shown in TABLE 1.

TABLE 1

| MATERIALS | Abbreviation | Product Name | Manufacturer Name | Compound Name | Remarks | Water Solubility | EO group | MW | Number of moles of EO | EO mass % |
|---|---|---|---|---|---|---|---|---|---|---|
| Monomer | M280 | M280 | MIWON | polyethylene glycol (400) diacrylate | | YES | YES | 508 | 9 | 78 |
| | M282 | M282 | MIWON | polyethylene glycol (200) diacrylate | | YES | YES | 308 | 4 | 57 |
| | VEEA | VEEA | NIPPON SHOKUBAI CO., LTD. | 2-(2-vinyloxy ethoxy) ethyl acrylate | | YES | YES | 200 | 2 | 44 |
| | ACMO | ACMO | KJ Chemicals Corporation | N,N-acryloylmorpholine | | YES | NO | 99 | — | — |
| | UA | UA-510H | KYOEISHA CHEMICAL Co., LTD. | dipentaerythritol pentaacrylate hexamethylene diisocyanate urethane prepolymer | | — | — | — | — | — |
| | ATM | ATM-35E | Shin Nakamura Chemical Co., Ltd. | ethoxylated pentaerythritol tetraacrylate | | — | — | — | — | — |
| | DPE | LIGHT ACRYLATE DPE-6A | KYOEISHA CHEMICAL Co., LTD. | dipentaerythritol hexaacrylate | | — | — | — | — | — |
| | DM | DMAA | KJ Chemicals Corporation | dimethyl acrylamide | | — | — | — | — | — |
| | ATMM3LMN | A-TMM-3LM-N | Shin Nakamura Chemical Co., Ltd. | pentaerythritol triacrylate | | NO | NO | — | — | — |
| Anti-smear Agent | MT70 | FOMBLIN® MT70 | SOLVAY | perfluoropolyether derivative; 80% methyl ethyl ketone (solvent); 20% | polymerizable, tetrafunctional used after substituted with ACMO | NO | unknown | 3000 | — | — |
| | FAAC6 | CHEMINOX FAAC-6 | UNIMATEC Co., Ltd. | 2-(perfluorohexyl)ethyl acrylate | polymerizable | NO | NO | 418 | — | — |
| | DAC | OPTOOL DAC-HP | DAIKIN INDUSTRIES, LTD. | modified perfluoropolyether (PFPE) | polymerizable | — | — | — | — | — |
| | DL100 | POEM DL-100 | RIKEN VITAMIN Co., Ltd. | diglycerol monolaurate (fatty acid ester) | | — | unknown | — | — | — |
| Polymerization Initiator | OXE02 | IRGACURE OXE02 | BASF | ethanone,1-[9-ethyl-6-(2-methyl benzoyl)-9H-carbazole-3-yl]-, 1-(O-acetyl oxime) | | — | — | — | — | — |
| | 2959 | Omnirad 2959 | IGM Resins | 1-[4-(2-hydroxyethoxy)-phenyl]-2-hydroxy-2-methyl-1-propane-1-one | | — | — | — | — | — |
| | 819 | IRGACURE 819 | IGM Resins | bis(2,4,6-trimethyl-benzoyl)-phenyl-phosphine oxide | | — | — | — | — | — |
| | TPO | IRGACURE TPO | IGM Resins | diphenyl(2,4,6-trimethyl-benzoyl) phosphine oxide | | — | — | — | — | — |

As the synthetic polymer film, for example, the synthetic polymer film disclosed in Patent Document No. 8 can be used. The blend of the materials used in the UV-curable resin for formation of the synthetic polymer film of Example 1 is shown in TABLE 2. TABLE 3 shows the evaluation results of the film surface (the surface of the synthetic polymer film). Example 1 corresponds to Example 1 disclosed in Patent Document No. 8. The evaluation method is the same as that employed in Example 2 and Example 3 which will be described later.

TABLE 2

| | Monomer | | | | | Polymerization Initiator | Anti-smear Agent |
|---|---|---|---|---|---|---|---|
| | UA | ATM | DPE | DM | ACMO | 819 | DAC |
| Example 1 | 8.0% | 45.0% | 18.5% | 24.0% | 1.5% | 2.0% | 1.0% |

TABLE 3

| | | Film Surface Properties | | |
|---|---|---|---|---|
| | | Water Contact Angle (°) | Hexadecane Contact Angle (°) | |
| | Adhesion | Immediately After Dropped | Immediately After Dropped | 10 sec |
| Example 1 | Excellent | 158.0 | 66.0 | 31.0 |

The synthetic polymer film of Example 1 contains a polymerizable fluoric compound as the anti-smear agent. DAC-HP (manufactured by DAIKIN INDUSTRIES, LTD.) used herein has two polymerizable functional groups. The molecular weight is 1169 to 1999, and the proportion of the contained fluorine element is 24.4 mass % to 42.8 mass % (all these numbers are estimates). The synthetic polymer film of Example 1 has a very high static contact angle of water, 158.0°, and has ultrahydrophobicity. The synthetic polymer film of Example 1 has a very high static contact angle of hexadecane, 66.0°, and has excellent oil repellency.

[Improvement of Synthetic Polymer Film]

According to research conducted by the present inventors, it was found that a conventional synthetic polymer film such as disclosed in Patent Document No. 8 sometimes changed the pH of water (aqueous solution) adhered to the surface of the film. Since the diameter of the endoscope distal end cover is not more than about 10 mm, it is estimated that the influence on a human body or the like is small, but it is preferred that it does not affect the pH. In view of such, the present inventors studied a synthetic polymer film of which the water repellency and oil repellency are further improved and which less affects the pH of water (aqueous solution) adhered to the surface of the film.

As a result, the present inventors found that, when a synthetic polymer film 13 which has the above-described surface structure is produced using a photocurable resin which contains a polymerizable fluoric compound which has a plurality of polymerizable functional groups, the surface of the resultant synthetic polymer film has further improved water repellency and oil repellency, and the influence on the pH of water (aqueous solution) on the surface is small. It was also found that, when the photocurable resin further contains a monofunctional polymerizable fluoric compound, the resultant synthetic polymer film can have further improved water repellency and oil repellency.

Some of the polymerization initiators produce an organic acid through photodecomposition (e.g., 819). To further reduce the influence on the pH of water (aqueous solution) adhered to the surface, using a polymerization initiator which does not produce an organic acid through photodecomposition is preferred. As the polymerization initiator which does not produce an organic acid, not only OXE02: ethanone,1-[9-ethyl-6-(2-methyl benzoyl)-9H-carbazole-3-yl]-,1-(O-acetyl oxime) and 2959: 1-[4-(2-hydroxyethoxy)-phenyl]-2-hydroxy-2-methyl-1-propane-1-one but also, for example, Omnirad 127 (IGM Resins): 2-hydroxy-1-{4-[4-(2-hydroxy-2-methyl-propionyl)-benzyl]phenyl}-2-methyl-propan-1-one can be suitably used. These polymerization initiators, advantageously, do not cause coloring or emission of a smell.

The small influence on the pH of water (aqueous solution) on the surface means that, for example, at the lapse of 5 minutes since placing a 200 µL drop of water on the surface of the synthetic polymer film, the pH of the aqueous solution is not less than 6.5 and not more than 7.5. A synthetic polymer film which has such characteristics is disclosed in Japanese Laid-Open Patent Publication No. 2019-156879 of the present applicant. The entire disclosure of Japanese Laid-Open Patent Publication No. 2019-156879 is incorporated by reference in this specification.

Of the "Anti-smear Agents" shown in TABLE 1, MT70 and FAAC6 contain a fluorine element and are polymerizable. Anti-smear agent MT70 has a plurality of polymerizable functional groups. That is, MT70 is a polyfunctional polymerizable fluoric compound. MT70 has a urethane methacrylate group. The number of polymerizable functional groups included in MT70 is four. The molecular weight (MW) of MT70 in TABLE 1 represents the weight average molecular weight measured by GPC with a calibration with polystyrene standards.

Anti-smear agent FAAC6 is a monofunctional polymerizable fluoric compound. That is, FAAC6 has one polymerizable functional group. The chemical structural formula of FAAC6 is shown at [CHEMICAL FORMULA 1].

[CHEMICAL FORMULA 1]

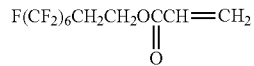

As the sample film which includes a base film 12A and a synthetic polymer film 13A provided on the base film 12A, Example 2 and Example 3 were produced. The blend composition of the materials of the respective synthetic polymer films and the type of the base film are shown in TABLE 4.

As the base film 12A, a 50 µm thick PET (polyethylene terephthalate) film ("A4300" manufactured by TOYOBO CO., LTD.), an 80 µm thick TAC (triacetyl cellulose) film ("TAC-TD80U" manufactured by FUJIFILM) or a 110 µm thick PC (polycarbonate) film ("Iupilon KS3410UR" manufactured by Mitsubishi Engineering-Plastics Corporation (Iupilon is a registered trademark)) was used.

Each of the sample films was produced using a moth-eye mold through the following process.

For the moth-eye mold, an aluminum film (thickness: about 1 µm) was formed on a glass substrate (about 5 cm×about 5 cm), and anodization and etching were alternately and repeatedly performed on this aluminum film, whereby a porous alumina layer ($D_p$: about 200 nm, $D_{int}$: about 200 nm, $D_h$: about 150 nm) was formed. Since the porous alumina layer has a structure obtained by inverting the moth-eye structure of the synthetic polymer film 13A, corresponding parameters which define the dimensions may sometimes be designated by the same symbols. Thereafter, a mold releasing treatment (also referred to as "die releasing treatment") was performed on the surface of the moth-eye mold (the surface which has the inverted moth-eye structure). The die releasing treatment broadly includes the treatment of applying a mold releasing agent to a surface of a die (herein, the surface of the moth-eye mold). Herein, a fluoric mold releasing agent (OPTOOL DSX (modified perfluoropolyether (PFPE)) manufactured by DAIKIN INDUSTRIES, LTD) was used as the mold releasing agent and was applied to the surface of the moth-eye mold by an immersion method. Note that four types of fluoric mold releasing agents were used, which contain a fluoric mold releasing component and a fluoric solvent with different mold releasing component concentrations. The standard concentration was 0.1%, low concentration I was 0.001%, low concentration II was 0.0001%, and low concentration III was 0.00001%. In either case, the concentration was represented in mass %. Commercially-available OPTOOL DSX has an effective component concentration of 20% and diluted with a fluoric solvent (perfluorohexane or the like) to a predetermined concentration when used. In dilution for the concentration adjustment, a fluoric solvent manufactured by Fluoro Technology (product name: diluent ZV) was used. As will be described later with experimental examples, the water repellency and oil repellency of the surface of the synthetic polymer film can be adjusted by treating the surface of the moth-eye mold with mold releasing agents of different concentrations.

The UV-curable resin applied to the surface of the base film 12A was irradiated with ultraviolet light (UV) with the moth-eye mold being pressed against the base film 12A, whereby the UV-curable resin was cured. Thereafter, the moth-eye mold was separated from the base film 12A, whereby a synthetic polymer film 13A to which the inverted moth-eye structure of the moth-eye mold was transferred was formed on the surface of the base film 12A. The exposure amount was about 200 mJ/cm$^2$ (on the basis of light at the wavelength of 375 nm). In each sample film, $D_p$ was about 200 nm, $D_{int}$ was about 200 nm, and $D_h$ was about 150 nm. In each sample, the synthetic polymer film was produced without using a solvent. In the ultraviolet light irradiation, a UV lamp manufactured by Fusion UV Systems (product name: LIGHT HANMAR6J6P3) was used.

When the PC film was used as the base film 12A (Example 3), a UV-curable resin was applied to the moth-eye mold while the moth-eye mold was heated to 20° C. or 40° C. on a heat stage. On the moth-eye mold to which the UV-curable resin was applied, the PC film was placed and evenly pressed against the mold using a hand roller. Then, the UV-curable resin was irradiated with ultraviolet light from the PC film side so as to be cured, whereby the sample film including the synthetic polymer film on the PC film was obtained. The process of producing the synthetic polymer film on the PC film is also referred to as "transfer process". The temperature in that process (20° C. or 40° C.) is also referred to as "transfer temperature".

The evaluation results of respective sample films of Example 2 and Example 3 as to the properties of the sample films, the adhesion between the synthetic polymer film and the base film, and the properties of the surfaces of the sample films (i.e., the surfaces of the synthetic polymer films) are shown in TABLE 5A. Note that the films of Example 2 and Example 3 shown in TABLE 5A were produced by performing the above-described die releasing treatment using the mold releasing agent of the standard concentration. Sample films produced by performing the die releasing treatment carried out in production of a synthetic polymer film which had the same composition as Example 2 with the use of the mold releasing agent of low concentrations I, II and III were also subjected to the same evaluations, and the evaluation results are shown below in TABLE 5B. In TABLE 5B, Examples 2A, 2B and 2C are sample films produced using the mold releasing agent of low concentrations I, II and III, respectively.

For the properties of the sample films, evaluation of coloring and smell of the sample films and identification of acid were carried out. The evaluated surface properties of the sample films were the spreadability of a water drop over the surface of the synthetic polymer film, the change of the pH of the water drop, and the static contact angle of water or hexadecane with respect to the surface.

[Evaluation of Sample Film Properties]

Coloring

Coloring of the sample films (the degree of yellowing) was visually observed.
- ○: Transparent with no color even when 10 sheets of the sample film were stacked up;
- Δ: Single sheet was transparent with no color, but yellowed portions were detected when 10 sheets of the sample film were stacked up;
- x: Yellowed portions were detected in a single sheet of the sample film.

Herein, when ○ or Δ, the sample film was judged to be usable.

Smell

The presence/absence (degree) of a smell of the sample films was evaluated as follows. A 5 cm×5 cm piece of the sample films was placed in a 100 mL glass container. The container was tightly closed and left in an incubator at 40° C. for 24 hours. After being left for 24 hours, five panelists smelled and evaluated the degree of the smell in the container immediately after the container was opened.
- ○: Panelists noticed a faint smell, but the smell was not unpleasant;
- Δ: Panelists noticed a smell, but the smell was not unpleasant;
- x: Panelists noticed an unpleasant smell.

Herein, when ○ or Δ, the sample film was judged to be usable.

[Evaluation of Adhesion to Base Film]

TABLE 4

| | Monomer | | | | Polymerization Initiator | | Anti-smear Agent | | Base Film |
|---|---|---|---|---|---|---|---|---|---|
| | M280 | M282 | VEEA | ACMO | OXE02 | 2959 | MT70 | FAAC6 | |
| Example 2 | 28.0% | 62.6% | | 2.8% | 1.9% | | 1.9% | 2.8% | TAC |
| Example 3 | 56.1% | | 37.4% | | | 1.9% | 1.9% | 2.8% | PC |

The adhesion of the synthetic polymer film to the base film was evaluated as described in the following paragraph.

In an environment where the temperature was 23° C. and the humidity was 50%, 11 vertical incisions and 11 horizontal incisions were formed in a surface of a synthetic polymer film of each sample film (a surface opposite to the base) using a utility knife at intervals of 1 mm in the shape of a grid such that 100 squares (1 mm on each side) were formed. Then, a polyester adhesive tape "No. 31B" manufactured by NITTO DENKO CORPORATION was placed on and pressed against the square portions. Thereafter, the adhesive tape was peeled off in a direction of 90° with respect to the surface of the square portions at a velocity of 100 mm/s. Thereafter, the surface state of the synthetic polymer film on the base was visually observed, and the number of squares from which the polymer layer on the base was not removed, M, was counted. When the PC film was used as the base film (Example 3), the evaluation was carried out at both transfer temperatures, 20° C. and 40° C., and the same results were obtained (the number of M was "100").

[Evaluation of Film Surface Properties]

Degree of Spread of Water Over Synthetic Polymer Film

Deionized water was adjusted to pH=7.0±0.1 using 0.01 mol/L hydrochloric acid solution and 0.011 mol/L sodium hydroxide solution. That is, neutral water was prepared in this way.

measurements at the three locations were averaged. Herein, the first measurement location was at a central portion of each sample film. The second and third measurement locations were away from the first measurement location by 20 mm or more and were in point symmetry with respect to the first measurement location. When the contact angle is not less than 150°, a liquid drop which was formed at the tip of a microsyringe and brought into contact with the surface sometimes failed to land on (move onto) the surface, i.e., remained at the tip of a microsyringe, so that the contact angle was unmeasurable. Such a case was indicated as "not landed". That is, "not landed" means that the contact angle was not less than 150°.

TABLE 5A

| | Film Properties | | | Water Diameter | pH | | Water Contact Angle (°) | | Hexadecane Contact Angle (°) | |
|---|---|---|---|---|---|---|---|---|---|---|
| | Adhesion | Color | Smell | (mm) | Method 1 | Method 2 | 1 sec | 10 sec | 1 sec | 10 sec |
| Example 2 | 100 | Δ | ○ | 8.0 | 6.8 | 6.9 | not landed | | 100.8 | 100.7 |
| Example 3 | 100 | ○ | ○ | 8.5 | 6.8 | 6.8 | not landed | | 100.1 | 99.8 |

On the surface of each sample film, a 0.2 cc (200 μL) drop of the above-described pH-adjusted water was placed using a micropipette. Thereafter, the maximum spread diameter (area equivalent circle diameter) up to 5 min was measured, and the average value for five measurements from each sample film was evaluated.

pH Measurement

The measurement of the pH was carried out as follows.

In the same way as that described above, on the surface of each sample film, a 0.2 cc (200 μL) drop of the above-described pH-adjusted water was placed using a micropipette. After the passage of 5 minutes, the aqueous solution (including water in which an extract from the synthetic polymer film was dissolved) on the surface of each sample film was measured using an electrode for flat samples which is described below, and the average value for five measurements from each sample film was evaluated (Method 1). Method 2 is different from Method 1 in that the above-described aqueous solution on the surface of each sample film was scooped up using a sampling sheet for measurement. Unless otherwise specified, Method 1 was used.

Electrode: pH electrode, product number: 0040-10D (semiconductor sensor) manufactured by HORIBA, Ltd.

Sampling sheet: sampling sheet B, product number: Y011A manufactured by HORIBA, Ltd.

Measurement of Static Contact Angle

The static contact angle of water and hexadecane with respect to the surface of the synthetic polymer film of each sample film was measured using a contact angle meter (PCA-1 manufactured by Kyowa Interface Science Co., Ltd). A drop of water or hexadecane (about 10 μL) was placed on the surface of the synthetic polymer film of each sample film. The static contact angle was measured at the lapse of 1 second, 10 seconds and 60 seconds since placing the water drop. The contact angle was measured at three locations by a θ/2 method (θ/2=arctan (h/r), θ: contact angle, r: radius of liquid drop, h: height of liquid drop), and the See the evaluation results of the sample films of Example 2 and Example 3 shown in TABLE 5A. Each of the curable resins for production of the synthetic polymer films of Example 2 and Example 3 includes a polyfunctional polymerizable fluoric compound. Each of Example 2 and Example 3 has excellent water repellency (the static contact angle of water is not less than 150°) and exerts a small influence on the pH of water (aqueous solution) on the surface. Further, each of Example 2 and Example 3 has excellent oil repellency (the static contact angle of hexadecane is not less than 100°).

The synthetic polymer films of Example 2 and Example 3 contain anti-smear agent MT70 and anti-smear agent FAAC6. The sample film of Example 2 includes a TAC film as the base film. In contrast, the sample film of Example 3 includes a PC film as the base film.

As disclosed in Japanese Laid-Open Patent Publication No. 2019-51638 of the present applicant, the present applicant found that a 2-(2-vinyloxy ethoxy)ethyl (meth)acrylate monomer was a promising candidate for the acrylic monomer which can improve adhesion with a PC film. The entire disclosures of Japanese Laid-Open Patent Publication No. 2019-51638 are incorporated by reference in this specification. If the proportion of a 2-(2-vinyloxy ethoxy)ethyl (meth)acrylate monomer unit contained in the cross-linked structure of a synthetic polymer film to the entirety of the synthetic polymer film is, for example, not less than 15 mass % and less than 45 mass %, the synthetic polymer film can have excellent PC adhesion. PC is a resin which generally exhibits high physical properties among engineering plastics and has been widely used particularly because of its excellent shock resistance and heat resistance.

In Example 3, VEEA manufactured by NIPPON SHOKUBAI CO., LTD. was used as the 2-(2-vinyloxy ethoxy)ethyl acrylate, and polymerization initiator 2959 was used. Example 3 has excellent adhesion with a PC film. Note that Example 2 in which a TAC film was used as the base film has acceptable adhesion with a TAC film.

The other examples of the PC film than those used in the above-described examples include "CARBOGLASS (registered trademark)" manufactured by AGC Inc., "PUREACE (registered trademark)" manufactured by TEIJIN LIMITED, and "Makrofol (registered trademark)" manufactured by Covestro.

In the foregoing, an example of a multilayer film including a polycarbonate film and a synthetic polymer film wherein the polycarbonate film was used as the base film has been described, although the present invention is not limited to this example. For example, a plastic molded product of polycarbonate can be used as the plastic base. In this case, a moth-eye mold may be used which is manufactured using an aluminum film deposited on a glass base of a desired shape.

By laminating a molded product of various shapes with a multilayer film which includes a polycarbonate film and a synthetic polymer film, excellent water repellency and excellent oil repellency can be given to the surface of the molded product of various shapes, and a surface can be realized which exerts a small influence on the pH of water (aqueous solution) on the surface.

As illustrated with the experimental examples, when a synthetic polymer film is formed from a curable resin which contains a polymerizable fluoric compound which has a plurality of polymerizable functional groups, the synthetic polymer film can have excellent water repellency and excellent oil repellency. Such a synthetic polymer film is also excellent in durability of the water repellency and oil repellency at the surface.

The polymerizable fluoric compound which has polymerizable functional groups includes, for example, a fluorine-containing hydrocarbon chain and a (meth)acrylate group at the terminal. The fluorine-containing hydrocarbon chain is likely to reside near the surface of curable resin. A synthetic polymer film which is realized by curing such a curable resin has excellent water repellency and excellent oil repellency.

Refer to the evaluation results of the sample films of Examples 2A, 2B and 2C shown in TABLE 5B. As the concentration of the mold releasing agent used in the die releasing treatment decreases, the water repellency decreases, although each of the sample films has excellent water repellency and excellent oil repellency. When the surface of the moth-eye mold is treated with a fluoric mold releasing agent, the proportion of the fluorine element contained near the surface of the synthetic polymer film can further increase. Thus, such a treatment is more preferred from the viewpoint of excellent water repellency and excellent oil repellency. The water repellency and oil repellency of the synthetic polymer film can be adjusted by adjusting the concentration of the mold releasing agent. For achieving excellent water repellency and excellent oil repellency, it is preferred that the concentration of the mold releasing agent is, for example, not less than 0.001% (Example 2A).

In order that the polyfunctional polymerizable fluoric compound exhibits excellent water repellency and excellent oil repellency, it is preferred that the length (volume) of the fluorine-containing hydrocarbon chain has an appropriate size. If the length (volume) of the fluorine-containing hydrocarbon chain is excessively large, it is sometimes difficult for the fluorine-containing hydrocarbon chain to move to the vicinity of the surface of the synthetic polymer film. As illustrated with the experimental examples, this problem can be solved by using together a monofunctional polymerizable fluoric compound which has a relatively lower molecular weight. If the length (volume) of the fluorine-containing hydrocarbon chain is excessively large, the solubility of the polymerizable fluoric compound to the other monomers of the curable resin decreases, and curing the curable resin sometimes results in a whitened synthetic polymer film.

For example, it is preferred that the polyfunctional polymerizable fluoric compound has a molecular weight of not less than 1000 and not more than 5000 and the proportion of the fluorine element contained in the polyfunctional polymerizable fluoric compound is not less than 20 mass % and not more than 60 mass %. The molecular weight of the polyfunctional polymerizable fluoric compound is more preferably not less than 2000 and not more than 4000, and the proportion of the fluorine element contained in the polyfunctional polymerizable fluoric compound is more preferably not less than 30 mass % and not more than 50 mass %. A polyfunctional polymerizable fluoric compound which has a relatively large molecular weight such as described above preferably has two, three or four polymerizable functional groups, for example.

Examples of the polyfunctional polymerizable fluoric compound, other than those used in the above-described examples, include "AD1700" manufactured by SOLVAY, "Y-1200" and "X-71-1203M" manufactured by Shin-Etsu Chemical Co., Ltd., "MEGAFACE RS-72-K", "MEGAFACE RS-75", "MEGAFACE RS-76-E", "MEGAFACE RS-76-NS" and "MEGAFACE RS-77" manufactured by DIC Corporation, and "EBECRYL8110" manufactured by DAICEL-ALLNEX LTD.

For example, "AD1700" manufactured by SOLVAY is poly(tetrafluoroethylene oxide-co-difluoromethylene oxide) with four functional groups at the terminal. The weight average molecular weight measured by GPC with a calibration with polystyrene standards is 3,500.

As illustrated with the experimental examples, when the curable resin used for formation of the synthetic polymer film further contains a monofunctional polymerizable fluoric compound, the synthetic polymer film can have more excellent water repellency and more excellent oil repellency. It is preferred that the molecular weight of the monofunctional polymerizable fluoric compound is not less than 100 and not more than 1000 and the proportion of the fluorine element contained in the monofunctional polymerizable fluoric compound is not less than 40 mass % and not more than 70 mass %. It is more preferred that the molecular weight of the

TABLE 5B

| | Film Properties | | | Water Diameter (mm) | pH | | Water Contact Angle (°) | | Hexadecane Contact Angle (°) | |
|---|---|---|---|---|---|---|---|---|---|---|
| | Adhesion | Color | Smell | | Method 1 | Method 2 | 1 sec | 10 sec | 1 sec | 10 sec |
| Example 2A | 100 | Δ | ○ | 8.1 | 6.8 | 6.8 | 128.1 | 127.6 | 64.3 | 35.1 |
| Example 2B | 100 | Δ | ○ | 8.3 | 6.8 | 6.9 | 101.2 | 98.5 | 31.4 | 15.3 |
| Example 2C | 100 | Δ | ○ | 8.3 | 6.8 | 6.9 | 94.3 | 89.6 | 19.6 | 10.1 | monofunctional polymerizable fluoric compound is not less than 300 and not more than 500. It is more preferred that the proportion of fluorine contained in the monofunctional polymerizable fluoric compound is not less than 50 mass % and not more than 60 mass %.

Examples of the monofunctional polymerizable fluoric compound, other than those used in the above-described examples, include "CHEMINOX FAMAC-4" and "CHEMINOX FAMAC-6" manufactured by UNIMATEC Co., Ltd. and Product ID "C8ACRY", "C8MTCRY", "C10ACRY" and "C10MTCRY" manufactured by Exfluor Research Corporation.

In the experimental examples, the polymerizable fluoric compound is referred to as "anti-smear agent", although the present invention is not limited to this example. A fluoric compound which meets the above-described conditions may be used.

The thus-produced synthetic polymer films of the above-described embodiments have a surface which is excellent in water repellency and oil repellency and exerts a small influence on the pH of water (aqueous solution) on the surface. Further, the synthetic polymer films have an anti-reflection function (for example, reflectance of 0.2% or less) and, therefore, a large amount of light can be guided to the observation window as compared with the conventional systems.

Since the surface of the above-described synthetic polymer film is excellent in water repellency and oil repellency, adhesion of blood and body fluid to the surface is suppressed. An example of the experimental results is shown below.

In the experiment, the following sample films were used:

Example Film 1 and Example Film 2 with the moth-eye surface, which were respectively produced using the UV-curable resins of Example 2 and Example 3 described above and using PET as the base;

Comparative Example Film 1 and Comparative Example Film 2 without the moth-eye surface (i.e., with a flat surface), which were respectively produced using the UV-curable resins of Example 2 and Example 3 described above and using PET as the base;

Comparative Example Film 3 with the moth-eye surface and Comparative Example Film 4 without the moth-eye surface (i.e., with a flat surface), which were respectively produced using the UV-curable resin of Comparative Example 1 whose composition is shown in TABLE 6 below and using PET as the base;

Comparative Example Film 5 with the moth-eye surface, which was produced using the UV-curable resin of Comparative Example 2 whose composition is shown in TABLE 6 below and using PET as the base; and Comparative Example Film 6 which was the PET film itself.

The UV-curable resins of Comparative Example 1 and Comparative Example 2 were hydrophilic. The static contact angle of water with respect to Comparative Example Film 3 and Comparative Example Film 5 that had the moth-eye surface was less than 90°. The static contact angle of hexadecane with respect to Comparative Example Film 3 and Comparative Example Film 5 that had the moth-eye surface was less than 60°.

TABLE 6

| | Monomer | | | | | Initiator | | | Mold Releasing Agent | Base |
|---|---|---|---|---|---|---|---|---|---|---|
| | UA7100 | M280 | M282 | ACMO | ATMM3LMN | OXE02 | 819 | TPO | DL100 | Film |
| Comparative Example 1 | | 47.5% | 47.5% | 2.9% | | 1.0% | | | 1.0% | PET |
| Comparative Example 2 | 50.3% | | | 29.1% | 17.7% | | 1.5% | 1.5% | | PET |

Example Film 1 and Example Film 2 and Comparative Example Film 1 through Comparative Example Film 6 were evaluated as to adhesion of blood. Herein, sheep blood (whole blood) was used instead of human blood. Adhesion of the sheep blood to the surfaces of the synthetic polymer films were evaluated as described below.

[Test Method]
1. Each film was placed such that the surface faces upward with a slant of about 20°.
2. One 15 μL drop of sheep whole blood was dropped from above the film, and it was checked whether the blood flows down to the lower part of the film or stays on the film.
3. The procedure of Step 2 was repeated five times in the same way, and it was counted how many times the blood stayed on the film.
4. 1-2 mL PBS (phosphate buffered saline) was poured over the drop of the blood, and the washability was evaluated.

The evaluation results are shown in TABLE 7A below.

TABLE 7A

| Sample Films | Material | Surface Shape | Number of adhered drops/5 drops | PBS Washing |
|---|---|---|---|---|
| Example Film 1 | Example 2 | moth-eye | 2 | Blood was cleanly washed away. |

TABLE 7A-continued

| Sample Films | Material | Surface Shape | Number of adhered drops/5 drops | PBS Washing |
|---|---|---|---|---|
| Comparative Example Film 1 | | flat | 5 | Unclear mixture of water and blood spread. |
| Example Film 2 | Example 3 | moth-eye | 1 | Blood was cleanly washed away. |
| Comparative Example Film 2 | | flat | 5 | Unclear mixture of water and blood spread. |
| Comparative Example Film 3 | Comparative Example 1 | moth-eye | 5 | Unclear mixture of water and blood spread. |
| Comparative Example Film 4 | | flat | 5 | Unclear mixture of water and blood spread but was somewhat flowable. |
| Comparative Example Film 5 | Comparative Example 2 | moth-eye | 5 | Unclear mixture of water and blood spread. |
| Comparative Example Film 6 | PET | flat | 5 | Unclear mixture of water and blood spread. |

As seen from the results shown above, in Example Film 1 and Example Film 2, the blood was unlikely to adhere, and the blood was easily washed away. That is, when the contact angle of water with respect to the moth-eye surface was not less than 150° and the contact angle of hexadecane with respect to the moth-eye surface was not less than 100°, the sheep blood hardly adhered to the surface and was easily washed away.

As seen from the results of Comparative Example Film 1 and Comparative Example Film 2, on the surface without the moth-eye structure, the washer liquid (PBS) and the blood were mixed together and not easily washed away. On Comparative Example Film 3 through Comparative Example Film 5 that have hydrophilic surfaces, the washer liquid and the blood were mixed together and not easily washed away even when the surfaces had the moth-eye structure. Also, on Comparative Example Film 6 that is a PET film, the washer liquid and the blood were mixed together and not easily washed away.

Next, the evaluation results of the sample films of Examples 2A, 2B and 2C are shown below in TABLE 7B.

TABLE 7B

| Sample Films | Material | Surface Shape | Number of adhered drops/5 drops | PBS Washing |
|---|---|---|---|---|
| Example Film 1A | Example 2A | moth-eye | 3 | Blood was cleanly washed away. |
| Comparative Example Film 1B | Example 2B | moth-eye | 5 | Unclear mixture of water and blood remained and adhered. |
| Comparative Example Film 1C | Example 2C | moth-eye | 5 | Unclear mixture of water and blood remained and adhered. |

As seen from the results shown above, for achieving an excellent blood adhesion suppressing effect, it is preferred that the concentration of the mold releasing agent is, for example, not less than 0.001% (Example 2A). Specifically, a synthetic polymer film with a surface where the contact angle of water (at the lapse of 10 seconds since the landing of the drop) with respect to the surface is not less than 128° and the contact angle of hexadecane (at the lapse of 10 seconds since the landing of the drop) with respect to the surface is not less than 35° can produce an excellent blood adhesion suppressing effect (see TABLE 5B). Note that the sample films of Example 2 and Example 3 which have been described in the foregoing section have extremely high water repellency and oil repellency so that the contact angle of water was not able to be measured. As for the contact angle of hexadecane, no significant difference was found between the value measured at the lapse of 1 second since the landing of the drop and the value measured at the lapse of 10 seconds since the landing of the drop, although the contact angle usually decreases with the passage of time. Therefore, when the contact angle changes over time, it is preferred from the viewpoint of reproducibility or the like that the value measured at the lapse of 10 seconds since the landing of the drop is used as the index.

Next, specific configuration examples of the endoscope distal end cover of an embodiment of the present invention are described with reference to FIG. 3 through FIG. 6. As a matter of course, the endoscope distal end cover of an embodiment of the present invention is not limited to those illustrated below.

FIG. 3(a), FIG. 3(b) and FIG. 3(c) are cross-sectional views schematically showing endoscope distal end covers 10A, 10B and 10C, respectively, of embodiments of the present invention.

The endoscope distal end cover 10A shown in FIG. 3(a) includes a synthetic polymer film 13, a base film 12 provided on the endoscope 20 side of the synthetic polymer film 13, and a cover film 16 provided on the endoscope 20 side of the base film 12, which serves as the cover member 16. The base film 12 and the synthetic polymer film 13 provided on the base film 12 constitute a film 14 which has a moth-eye structure over the surface.

The cover film 16 has greater tensile elongation than the base film 12. For example, the tensile elongation of the cover film 16 is preferably not less than 100%, more preferably not less than 200%, and still more preferably not less than 300%. The cover film 16 of high flexibility is in close contact with the end face of the endoscope distal end 20*t* (see FIG. 1(*b*)) and is arranged so as to cover the distal end 20*t*. The thickness of the cover film 16 is, for example, not more than 500 μm and is preferably not more than 300 μm. The thickness does not have a particular lower limit but is preferably not less than 100 μm in consideration of strength and/or handleability.

The base film 12 and the cover film 16 are bonded together using, for example, a known adhesive agent for optical purposes (adhesive layer 15). The refractive index of the adhesive layer 15 is preferably close to those of the base film 12 and the cover film 16. As a matter of course, the adhesive layer 15 is preferably transparent. The transmittance for visible light of the adhesive layer 15 is preferably not less than 80%, more preferably not less than 90%.

The cover film 16 that is arranged so as to cover the endoscope distal end 20*t* is secured at the lateral surface of the distal end 20*t* using, for example, a stretchable medical tape (not shown). In this case, to prevent a body fluid or blood from entering through a gap between the cover film 16 and the endoscope distal end 20*t*, the edge of the cover film 16 is assuredly covered with the medical tape, and the medical tape is assuredly adhered to the lateral surface of the endoscope distal end 20*t*.

Figure 3:
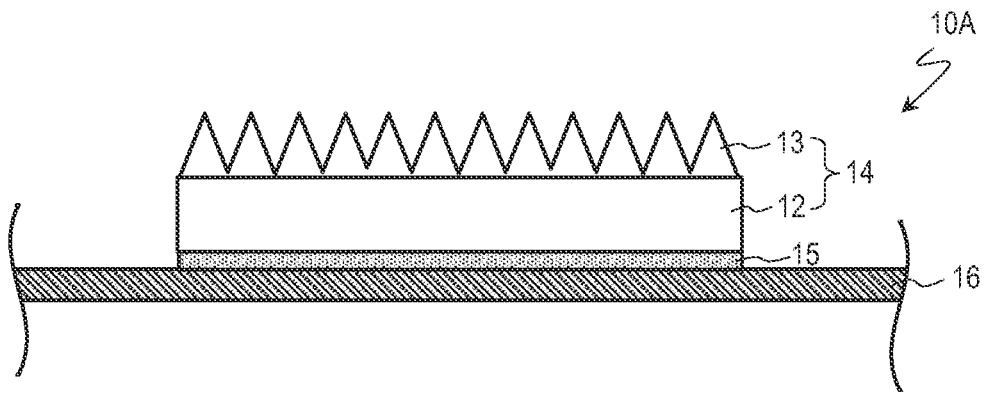
FIG. 3(a), FIG. 3(b) and FIG. 3(c) are cross-sectional views schematically showing endoscope distal end covers 10A, 10B and 10C, respectively, of an embodiment of the present invention.
Figure 3:
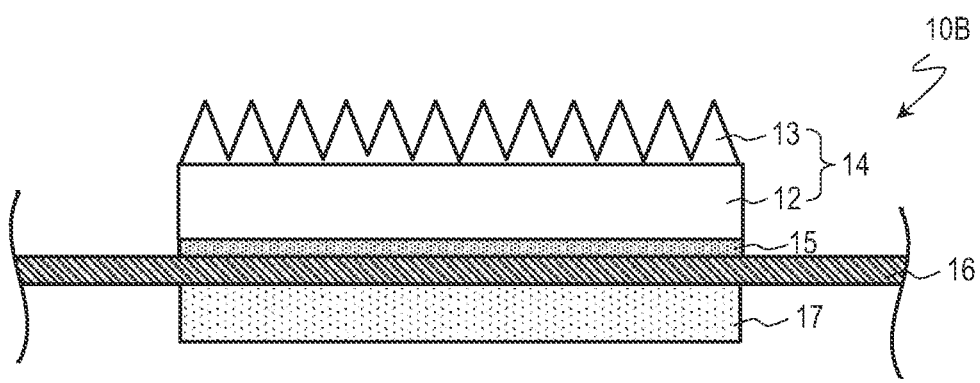
Figure 3:
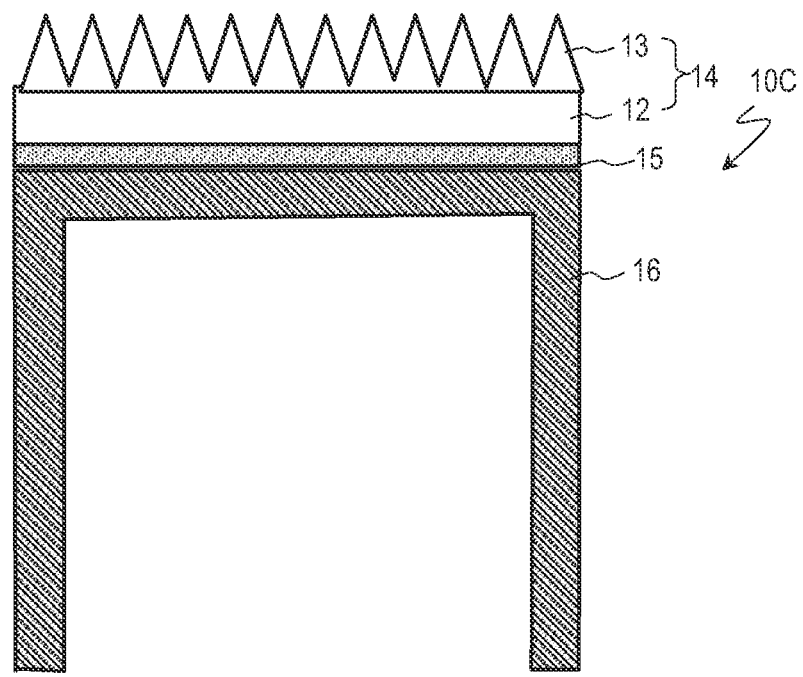
Figure 6:
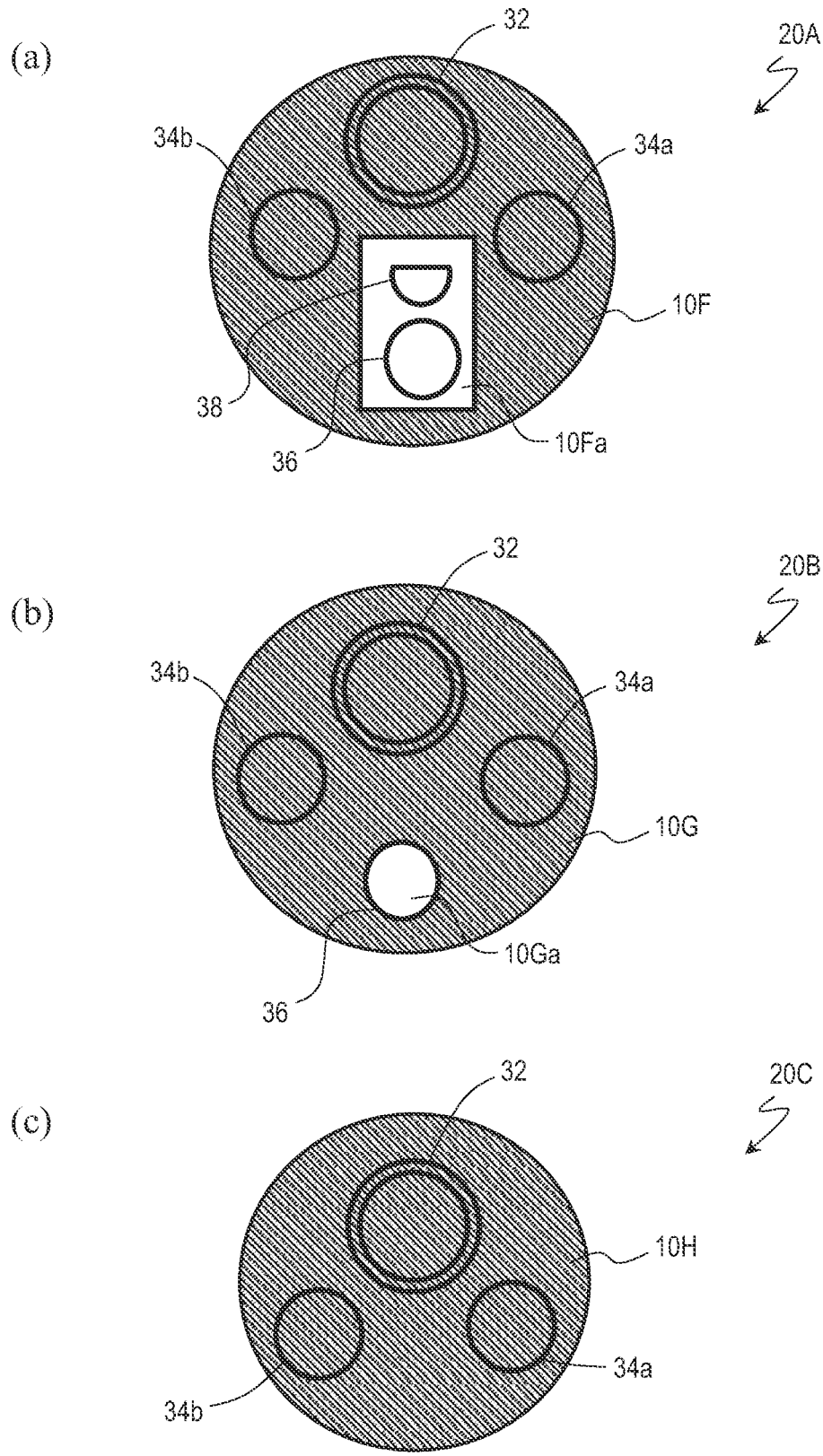
FIG. 6(a), FIG. 6(b) and FIG. 6(c) are schematic diagrams showing an end face of the distal end of endoscopes 20A, 20B and 20C, respectively, of an embodiment of the present invention.

The endoscope distal end cover 10B shown in FIG. 3(*b*) also includes a cover film 16 as the cover member 16 as does the endoscope distal end cover 10A. The cover 10B further includes an adhesive layer 17 which is provided on the endoscope side of the cover film 16 in the cover 10A. The adhesive layer 17 is provided only over the end face of the endoscope distal end 20*t* as is the film 14 that has the moth-eye structure at the surface. As a matter of course, in some types of the endoscope 20, the adhesive layer 17 has an opening corresponding to the openings 10Fa or 10Ga as shown in FIG. 6(*a*) and FIG. 6(*b*).

The adhesive layer 17 is preferably made of a relatively-soft adhesive agent (including a pressure sensitive adhesive) for improving the adhesion to the endoscope distal end 20*t*. For example, an elastic adhesive agent which exhibits rubber elasticity when cured and an adhesive agent which has a closed cell structure (see, for example, Japanese Patent No. 6066390) can be used. When a relatively-soft adhesive agent is used, the adhesive agent can cover steps in the end face of the endoscope distal end 20*t*, so that the absence of air gaps (bubbles) between the adhesive layer 17 and the end face of the endoscope distal end 20*t* can be readily realized.

The cover member 16 of the endoscope distal end cover 10C shown in FIG. 3(*c*) has the shape of a cap (the shape of a hollow cylinder with one end being closed) rather than a film. The endoscope distal end 20*t* is accommodated in the inner space of this cap. That is, the cover 10C includes a cylindrical attaching portion which covers the lateral surface of the distal end 20*t* when the cover 10C is attached to the endoscope distal end 20*t*. It is preferred that the cover member 16 is made of, for example, the aforementioned elastomer, the cover member 16 has elasticity, and the cover member 16 is configured such that a straining force is exerted on the lateral surface of the endoscope distal end 20*t*.

Figure 4:
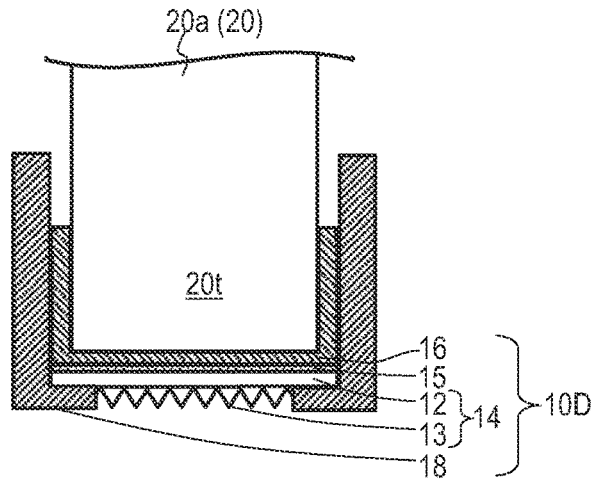
FIG. 4(a), FIG. 4(b) and FIG. 4(c) are cross-sectional views schematically showing endoscope distal end covers 10D, 10E and 10F, respectively, of an embodiment of the present invention.
Figure 4:
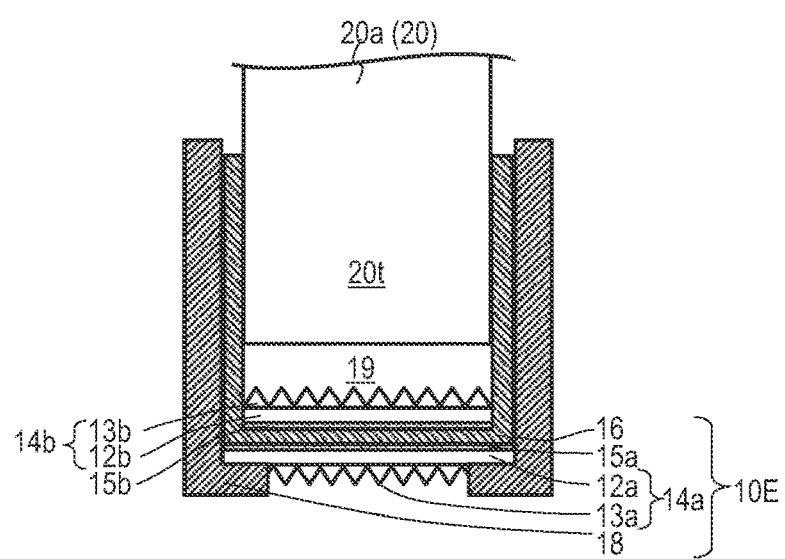
Figure 4:
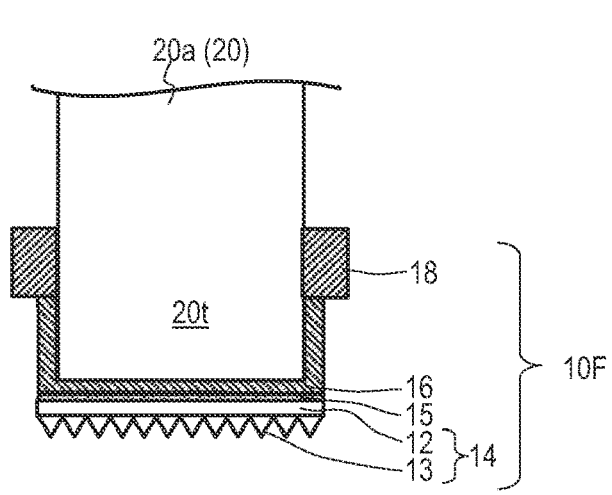

FIG. 4(*a*), FIG. 4(*b*) and FIG. 4(*c*) are schematic cross-sectional views of endoscope distal end covers 10D, 10E and 10F, respectively, of embodiments of the present invention.

Each of the covers 10D and 10E includes a cover film 16 as the cover member 16 and further includes a securing member 18 which includes a cylindrical attaching portion capable of pressing the cover member 16 against the lateral surface of the endoscope distal end 20*t*. The securing member 18 may include a portion capable of pressing the periphery of the upper surface of the film 14 against the end face of the endoscope distal end 20*t*. The securing member 18 can be made of, for example, the aforementioned elastomer as is the cover member 16 of the cover 10C shown in FIG. 3(*c*) which includes the cylindrical attaching portion.

The cover 10E shown in FIG. 4(*b*) includes, in addition to the synthetic polymer film 13*a* provided outside the cover film 16, another synthetic polymer film 13*b* provided on the endoscope 20 side of the cover member 16. The synthetic polymer films 13*a*, 13*b* each have the same configuration as the above-described synthetic polymer film and are formed on the base film 12*a*, 12*b* using, for example, a UV-curable resin. The base film 12*a*, 12*b* is adhered to the cover film 16 using, for example, an adhesive layer 15*a*, 15*b*.

The cover 10E is arranged such that an air layer 19 is formed between the synthetic polymer film 13*b* and the endoscope 20 (the distal end 20*t*). The securing member 18 of the cover 10E can also be made of, for example, the aforementioned elastomer as is the cover member 16 of the cover 10C shown in FIG. 3(*c*) which has the cylindrical attaching portion. The position of the cover 10E (the thickness of the air layer 19) may be, for example, indicated with a mark (line) in a portion of the perimeter of the lateral surface of the cover 10E which is coplanar with the end face of the distal end 20*t* when the cover 10E is attached, or may be indicated with a mark or step in the lateral surface of the endoscope 20. The thickness of the air layer 19 is not particularly significant although it is preferred that the synthetic polymer film 13*b* does not come into contact with the end face of the endoscope 20. If the synthetic polymer film 13*b* is in contact with the end face of the endoscope 20, there is a probability that the synthetic polymer film 13*b* will not sufficiently perform an antireflection function.

If an air layer is formed between the cover film 16 and the end face of the endoscope 20 when the cover 10D shown in FIG. 4(*a*) is attached to the endoscope 20, the amount of light to be guided to the observation window reduces due to reflection. In contrast, when the cover 10E shown in FIG. 4(*b*) is used, the loss of light is suppressed to a small amount even if an air layer is formed because the synthetic polymer film 13*b* functions as an antireflection film.

The securing member 18 is preferably configured so as not to easily fall off from the endoscope distal end 20*t* in order that, when inserted or pulled out through a trocar, part of the securing member 18 is prevented from being caught by the trocar and remaining in a body cavity. For example, likewise as in the cover 10D shown in FIG. 4(*a*), the securing member 18 can be configured so as to thinly cover the entirety of the endoscope 20 in the longitudinal direction of the endoscope 20, so that a smaller part of the securing member 18 can be caught by the trocar or the like. However, the securing member 18 is not limited to this example. So long as the cover member 16 is assuredly secured, part of the cover member 16 may be secured using a medical tape as the securing member 18 likewise as in the cover 10F shown in FIG. 4(*c*). Other than the medical tape, a cord or rubber may be used as the securing member 18 for securing. The securing member 18 may be a member which is stretchable like rubber, or may be a fastening device such as screw, hook, etc., provided between the endoscope distal end 20t and the cover member 16.

Figure 5:
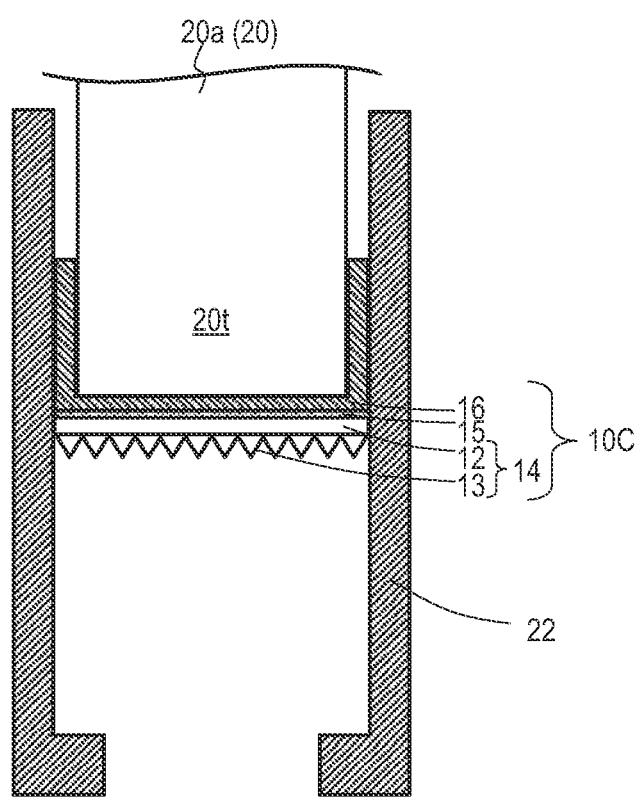
FIG. 5(a) and FIG. 5(b) are cross-sectional views schematically showing states of the endoscope distal end cover 10C of an embodiment of the present invention and an attachment 22 attached thereto.
Figure 5:
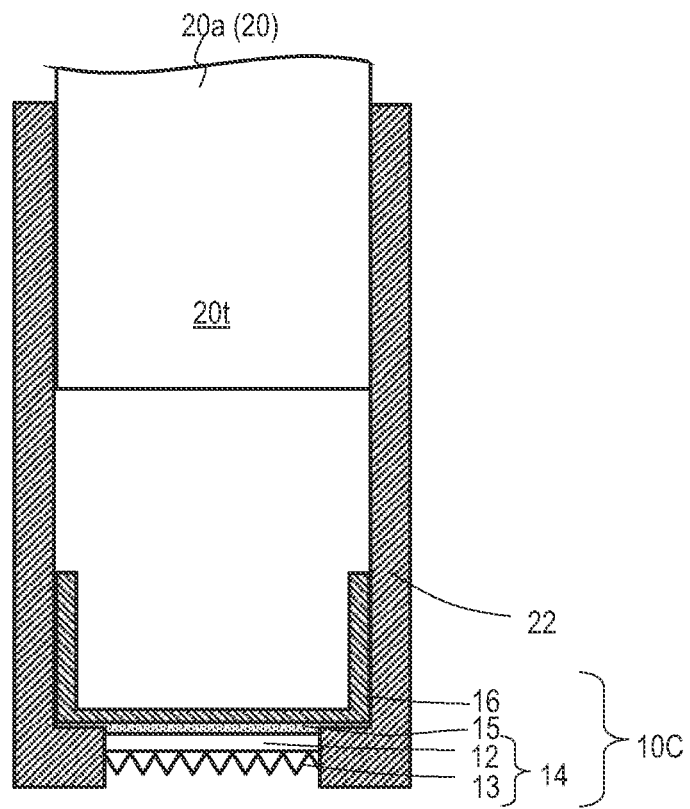

FIG. 5 shows schematic cross-sectional views showing states of the endoscope distal end cover 10C of an embodiment of the present invention and an attachment 22 attached thereto.

In attaching the cover 10C that has the cover film to the endoscope distal end 20t, for example, an attachment 22 for securing the field of view (space) for observation may be used instead of the above-described securing member 18. An attachment 22 which is made of a transparent elastomer is commercially available. The cover film 16 may be adhered to the endoscope distal end 20t using an adhesive agent as described above. Alternatively, the cover film 16 may not be adhered to the endoscope distal end 20t. For example, as shown in FIG. 5(b), the cover film 16 may be attached to the distal end of the attachment 22. Adhering the cover film 16 to the attachment 22 via the adhesive layer 15 is sometimes preferred rather than adhering the cover film 16 to the endoscope distal end 20t because the risk of forming scratches and smears on the observation window of the endoscope 20 decreases. The attachment 22 is secured to the distal end 20t using, for example, a stretchable medical tape.

The above-described methods for securing the endoscope distal end cover can be appropriately employed in combination. A configuration where synthetic polymer films are provided on opposite sides can be combined with the previously-illustrated structure.

Next, schematic diagrams showing an end face of the distal end of endoscopes 20A, 20B and 20C of an embodiment of the present invention are shown in FIG. 6(a) through FIG. 6(c). The above-described endoscope distal end covers are applicable to any of the endoscopes.

The endoscope 20A shown in FIG. 6(a) has, at the end face of the distal end 20t, an observation window 32, illumination windows 34a, 34b, a forceps opening 36 and an ejection nozzle 38. The observation window 32 is washed by spraying a washer liquid and/or compressed air from the ejection nozzle 38 against the observation window 32.

The endoscope distal end cover 10F has an opening 10Fa through which the forceps opening 36 and the ejection nozzle 38 are exposed. The other features of the endoscope distal end cover 10F are the same as those of any of the above-described covers.

The surface of the cover 10F has a moth-eye structure of the synthetic polymer film 13 and has excellent water repellency and excellent oil repellency so that a body fluid, blood or the like is unlikely to adhere to the surface. Even if a body fluid, blood or the like adheres to the surface, it will be easily removed by a washer liquid and/or compressed air from the ejection nozzle 38 and, therefore, the surfaces of the observation window 32 and the illumination windows 34a, 34b can be kept clean.

The endoscope 20B shown in FIG. 6(b) does not have an ejection nozzle. Therefore, the endoscope distal end cover 10G has an opening 10Ga through which the forceps opening 36 is exposed. The other features of the endoscope distal end cover 10G are the same as those of any of the above-described covers. Since the cover 10G has excellent water repellency and excellent oil repellency, a body fluid, blood or the like is unlikely to adhere to the cover 10G and, thus, it is not necessary to wash the cover 10G. By omitting the mechanism for washing, the endoscope 20B can have a smaller size than the endoscope 20A.

The endoscope 20C shown in FIG. 6(c) has only an observation window 32 and illumination windows 34a, 34b at the end face of the distal end 20t. Therefore, the endoscope distal end cover 10H does not have an opening and is arranged so as to cover the entirety of the end face of the distal end 20t.

As a matter of course, an endoscope of an embodiment of the present invention is not limited to those illustrated in this specification but can be variously modified.

[Liquid Film of Water-Repellent Oil Covering Surface of Synthetic Polymer Film]

In the endoscope distal end cover of the above-described embodiment, a liquid film of a water-repellent oil covering at least a portion of the synthetic polymer film located above the observation window is further provided, whereby the effect of suppressing adhesion of blood or body fluid to the observation window of the endoscope can be further improved, and the durability of the blood adhesion suppressing effect can be improved.

As the water-repellent oil, a silicone oil or a fluoric oil can suitably be used. As the silicone oil, a non-reactive silicone oil is preferred. For example, a dimethyl silicone oil (dimethyl siloxane with methyl groups at all of the side chains and termini) can be suitably used. The method of applying the water-repellent oil to the surface of the synthetic polymer film is not particularly limited, and known application methods are broadly applicable.

Figure 7:
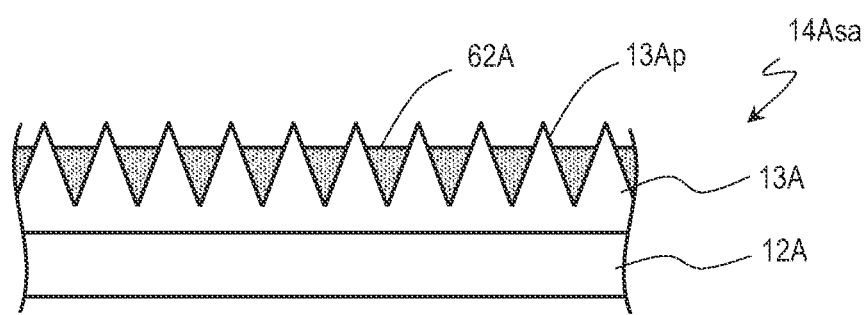
FIG. 7(a), FIG. 7(b) and FIG. 7(c) are diagrams schematically showing states of a film for use in an endoscope distal end cover of another embodiment of the present invention where a water-repellent oil is applied to a surface of the film.
Figure 7:
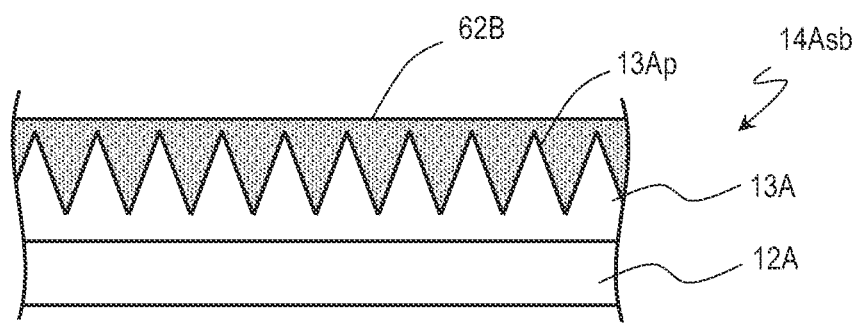
Figure 7:
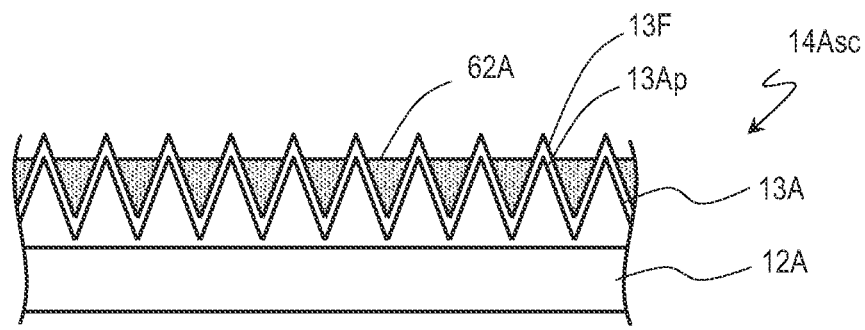

FIG. 7(a), FIG. 7(b) and FIG. 7(c) schematically show states where the water-repellent oil is applied to the surface of the film 14A shown in FIG. 2(a). As a matter of course, the present invention is not limited to these examples. The water-repellent oil may be applied to the surface of the film 14B shown in FIG. 2(b).

As in a film 14Asa shown in FIG. 7(a), the space between a plurality of raised portions 13Ap at the surface of the synthetic polymer film 13A is partially filled with a water-repellent oil 62A. Specifically, the surface of the water-repellent oil 62A may be lower than the plurality of raised portions 13Ap such that the tip ends of the plurality of raised portions 13Ap are projected above the surface of the water-repellent oil 62A. Alternatively, as in a film 14Asb shown in FIG. 7(b), a water-repellent oil 62B may be applied so as to cover the entirety of the plurality of raised portions 13Ap. Specifically, the surface of the water-repellent oil 62B may be higher than the plurality of raised portions 13Ap such that the tip ends of the plurality of raised portions 13Ap are present inside the layer of the water-repellent oil 62B.

When the water-repellent oil 62B covers the entirety of the plurality of raised portions 13Ap as in the film 14Asb shown in FIG. 7(b), the antireflection function of the plurality of raised portions 13Ap is lost. On the other hand, in the film 14Asa shown in FIG. 7(a), the tip ends of the plurality of raised portions 13Ap are projected above the surface of the water-repellent oil 62A and, therefore, the antireflection function is remained. Thus, whether the configuration that results after application of the water-repellent oil to the moth-eye surface is like the film 14Asa shown in FIG. 7(a) or the film 14Asb shown in FIG. 7(b) can be determined by observing with an eye the degree of surface reflection.

Still alternatively, as in a film 14Asc shown in FIG. 7(c), a water-repellent and oil-repellent layer 13F may be formed at the surface of the synthetic polymer film 13A, and the water-repellent oil 62A may be applied to the moth-eye surface that has the water-repellent and oil-repellent layer 13F. In the example described herein, the space between the plurality of raised portions 13Ap at the surface of the synthetic polymer film 13A is partially filled with the water-repellent oil 62A likewise as in the film 14Asa of FIG.

7(a), although the water-repellent oil 62B may be applied so as to cover the entirety of the plurality of raised portions 13Ap likewise as in the film 14Asb of FIG. 7(b).

When the water-repellent and oil-repellent layer 13F is formed at the moth-eye surface of the synthetic polymer film 13A as will be described later with experimental examples, the synthetic polymer film 13A may be hydrophilic. As a matter of course, from the viewpoint of stability or the like, it is preferred that the synthetic polymer film 13A has water repellency. The water-repellent and oil-repellent layer 13F can be formed using, for example, a fluoric coating material. A preferred thickness of the water-repellent and oil-repellent layer 13F is, for example, not less than 1 nm and not more than 50 nm, although it depends on whether the underlying synthetic polymer film 13A is hydrophilic or water-repellent and on the degree of hydrophilicity or water repellency.

The surface of the synthetic polymer film of the endoscope distal end cover of the above-described embodiment has excellent water repellency and excellent oil repellency, where the static contact angle of water (at the lapse of 10 seconds since the landing of the drop) with respect to the surface is not less than 128°, preferably not less than 150°, and the static contact angle of hexadecane (at the lapse of 10 seconds since the landing of the drop) with respect to the surface is not less than 35°, preferably not less than 60°. That is, a synthetic polymer film with the moth-eye surface where the static contact angle of water with respect to the surface is not less than 128° and the static contact angle of hexadecane with respect to the surface is not less than 35° can itself be used for the endoscope distal end cover, although in the present embodiment the water repellency and the oil repellency required for the surface of the synthetic polymer film may be lower than those required for the synthetic polymer film of the previously-described embodiment because the water-repellent oil is applied to the surface. Specifically, when a liquid film of the water-repellent oil is formed, the surface of the synthetic polymer film only needs the static contact angle of water (at the lapse of 10 seconds since the landing of the drop) to be not less than about 98° (more than 99°), and it is preferably not less than 103°. As a matter of course, as in the synthetic polymer films of the previously-described embodiment, it is preferred that the effect on the pH of water (aqueous solution) adhered to the surface is small. Thus, when the synthetic polymer film is formed using a photocurable resin, it is preferred to use the above-described polymerization initiators which does not produce an organic acid.

Hereinafter, as will be described with experimental examples, the water-repellent oil is preferably a silicone oil whose kinematic viscosity is lower than 350 mm$^2$/s (1 mm$^2$/s=1 cSt), more preferably a silicone oil whose kinematic viscosity is equal to or lower than 10 mm$^2$/s. In the description of the experimental examples which will be provided below, for the sake of distinguishment from Examples and Comparative Examples of the previously-described embodiment, "Example 2-" and "Comparative Example 2-" are prefixed and used only for comparison in the forms where the water-repellent oil was applied to the moth-eye surface. Therefore, even if a synthetic polymer film of an example of the previously-described embodiment is included, it can be referred to as "Comparative Example" in the following description. On the contrary, even if a synthetic polymer film of a comparative example in the description of the previously-described embodiment is included, it can be referred to as "Example" in the following description.

In the following experimental examples, the water-repellent materials used were the UV-curable resin of Example 2 described above (referred to as Water Repellency 2) and the water-repellent materials of Examples 2A, 2B and 2C shown in TABLE 5B (Water Repellency 2A, 2B, 2C), and the hydrophilic materials used were the UV-curable resin of Comparative Example 2 described above (referred to as Hydrophilicity 1) and the hydrophilic materials (Hydrophilicity 2, 3, 4) whose compositions are shown in TABLE 8. Source materials of the UV-curable resins of Hydrophilicity 2, 3, 4 are shown in TABLE 1 and TABLE 9. Additive PC-3662 is an antistatic agent manufactured by Marubishi Oil Chemical Corporation, which is a silicone oil containing lithium salts. The contact angles of the surfaces of the synthetic polymer films which were made of the UV-curable resins of Hydrophilicity 2, 3, 4 with respect to water (at the lapse of 1 second and 10 seconds since the landing of the drop) are shown in TABLE 10.

TABLE 8

| | Monomer | | | | Initiator | | Additive |
|---|---|---|---|---|---|---|---|
| | ND-DA | PE300 | 4HBA | ATMM3LMN | 819 | TPO | PC-3662 |
| Hydrophilicity 2 | 79.2% | — | — | 20.3% | 0.5% | — | — |
| Hydrophilicity 3 | — | 78.8% | — | 20.7% | 0.5% | — | — |
| Hydrophilicity 4 | — | — | 46.3% | 46.3% | 1.4% | 1.4% | 4.6% |

TABLE 9

| Product Name | Manufacturer Name | Compound Name |
|---|---|---|
| ND-DA | ND-DA | DKS Co. Ltd. | 1,9-nonanediol diacrylate |
| PE300 | PE-300 | DKS Co. Ltd. | polyethylene glycol (300) diacrylate |
| 4HBA | 4HBA | Nihon Kasei Co. Ltd. | 4-hydroxybutyl acrylate |

TABLE 10

| | Film | | Water Contact Angle (°) | |
|---|---|---|---|---|
| | Resin | Surface Shape | 1 sec | 10 sec |
| Comparative Example 2-6 | Hydrophilicity 2 | moth-eye | 97.2 | 81.5 |
| Comparative Example 2-7 | Hydrophilicity 3 | moth-eye | 49.9 | 49.3 |
| Comparative Example 2-8 | Hydrophilicity 4 | moth-eye | 36.7 | 35.4 |

Using these water-repellent or hydrophilic materials, sample films which had at the surface the moth-eye structure schematically shown in FIG. 2(a) ($D_p$ was about 200 nm, $D_{int}$ was about 200 nm, $D_h$ was about 150 nm) were produced by the previously-described method.

Also, another sample film was produced which had a water-repellent and oil-repellent layer 13F at the surface of the synthetic polymer film 13A likewise as in the film 14Asc shown in FIG. 7(c). Herein, synthetic polymer films were produced using a hydrophilic material (Hydrophilicity 1) in the same way as that described above, and thereafter, sample films of Comparative Example 2-12 and Example 2-14 were produced as follows.

Comparative Example 2-12: a fluoric coating material with the concentration of 0.01 mass % (FluoroSurf (registered trademark) manufactured by Fluoro Technology) was poured over a surface of a hydrophilic synthetic polymer film. Thereafter, the film was dried at room temperature for about one hour. Then, the above-described diluted fluoric coating material was poured over the entire surface, and the film was further kept at room temperature for about three hours (Hydrophilic 1Fd). That is, the diluted fluoric coating material was applied twice.

Example 2-14: The sample film was produced in the same way as Comparative Example 2-12 except that the concentration of the fluoric coating material was 0.1 mass % (Hydrophilic 1Fc).

The results of measurement of the contact angle of water with respect to the respective sample films are shown in TABLE 11.

TABLE 11

| Film | | | Water Contact Angle (°) | |
|---|---|---|---|---|
| Resin | Surface Shape | | 1 sec | 10 sec |
| Comparative Example 2-12 | Hydrophilicity 1Fd | moth-eye | 83.2 | 71.4 |
| Example 2-14 | Hydrophilicity 1Fc | moth-eye | 115 | 103.1 |

As the water-repellent oil, three types of dimethyl silicone oils whose kinematic viscosity was 10 mm²/s, 350 mm²/s and 500 mm²/s (KF-96-10cs, KF-96-350cs and KF-96-500cs manufactured by Shin-Etsu Chemical Co., Ltd.) were used.

The aforementioned silicone oils were applied to the surface of the sample films (synthetic polymer films) by any of the following three methods.

First, the sample film was adhered onto a raw glass plate using an adhesive agent such that the surface of the sample film was flat.

Then, drops of several mL of the silicone oil was placed on the surface of the sample film, and the glass plate was spun by a spinner at a predetermined rotational speed (200 rpm, 1000 rpm or 3500 rpm) for 12 seconds (Method 1: Spin coating method).

The silicone oil was poured over the entire surface of the sample film while the surface of the sample film adhered onto the raw glass plate was kept at 45° with respect to a horizontal direction, and then the sample film was left for 30 minutes (Method 2: Pour-over method).

The entire surface of the sample film adhered onto the raw glass plate was wiped with cloth soaked with the silicone oil (for example, wiping cloth which can be suitably used in a clean room (herein, Savina (registered trademark) manufactured by KB SEIREN, LTD. was used)) (Method 3: Cloth wiping method).

The sample films prepared as described above and the raw glass plate (see TABLE 12 below) were evaluated as to the blood adhesion suppressing effect and its durability as will be described below. Herein also, sheep blood (whole blood) was used instead of human blood as in the experiment for the previously-described embodiment.

Three types of tests described below were carried out.

(Test 1)

Each film was placed such that the surface faces upward with a slant of about 20°-30°. Six 20 μL drops of sheep whole blood were dropped from above the film, and it was checked whether the blood flowed down to the lower part of the film or stayed on the surface of the film.

(Test 2)

After TEST 1 was carried out, 2 mL PBS (phosphate buffered saline) was poured twice over the entire surface of a film with remaining blood, and it was checked whether or not the blood was washed away.

(Test 3)

After TEST 2 was carried out, TEST 1 was carried out again.

The blood adhesion suppressing effect and its durability were evaluated based on the following criteria. When in TEST 1 the blood dropped on the film surface flowed down to the lower part of the film, the blood adhesion suppressing effect was evaluated as being ⊚ (excellent). When two or less blood drops were adhered to the film surface in TEST 1 but easily washed away in TEST 2, the blood adhesion suppressing effect was evaluated as being ○ (good). When more than two blood drops were adhered to the film surface in TEST 1 but easily washed away in TEST 2, the blood adhesion suppressing effect was evaluated as being Δ (tolerable); otherwise, the blood adhesion suppressing effect was evaluated as being x (not tolerable). The durability of the blood adhesion suppressing effect was evaluated as being (excellent) when the blood adhesion suppressing effect achieved as a result of TEST 3 was equivalent to the blood adhesion suppressing effect achieved in TEST 1. When the achieved blood adhesion suppressing effect was equivalent to that of TEST 1 although a puddle or the like was found in the washing of TEST 2, the durability of the blood adhesion suppressing effect was evaluated as being ○ (good). When the achieved blood adhesion suppressing effect was equivalent to that of TEST 1 except for a location of adhered blood in TEST 1 where the blood adhesion suppressing effect was eliminated (a history of blood adhesion remains), the durability of the blood adhesion suppressing effect was evaluated as being Δ (tolerable). When there was no blood adhesion suppressing effect or the blood adhesion suppressing effect was eliminated, the durability of the blood adhesion suppressing effect was evaluated as being x (not tolerable).

The evaluation results of the blood adhesion suppressing effect and its durability are shown in TABLE 12, and the observation results in TEST 1, TEST 2 and TEST 3 are shown in TABLE 13 and TABLE 14.

TABLE 12

| | Base | Surface Shape | Silicone Oil | Application Method | Blood Adhesion Suppressing Effect | Durability of Effect |
|---|---|---|---|---|---|---|
| Comparative Example 2-1 | Raw Glass | flat | none | — | X | X |
| Comparative Example 2-2 | Raw Glass | flat | 10 mm$^2$/s | 1000 rpm/12 sec | ○ | X |
| Comparative Example 2-3 | Raw Glass | flat | 10 mm$^2$/s | Pour-over | ○ | X |
| Comparative Example 2-4 | Hydrophilicity 1 | moth-eye | none | — | △ | X |
| Comparative Example 2-5 | Hydrophilicity 1 | moth-eye | 10 mm$^2$/s | 1000 rpm/12 sec | ○ | X |
| Comparative Example 2-6 | Hydrophilicity 2 | moth-eye | 10 mm$^2$/s | 1000 rpm/12 sec | ○ | X |
| Comparative Example 2-7 | Hydrophilicity 3 | moth-eye | 10 mm$^2$/s | 1000 rpm/12 sec | ○ | X |
| Comparative Example 2-8 | Hydrophilicity 4 | moth-eye | 10 mm$^2$/s | 1000 rpm/12 sec | ○ | X |
| Comparative Example 2-9 | Water Repellency 2 | flat | 10 mm$^2$/s | 1000 rpm/12 sec | X | X |
| Comparative Example 2-10 | Water Repellency 2 | flat | 10 mm$^2$/s | Pour-over | X | X |
| Comparative Example 2-11 | Water Repellency 2 | moth-eye | none | — | ○ | △ |
| Comparative Example 2-12 | Hydrophilicity 1Fd | moth-eye | 10 mm$^2$/s | Pour-over | X | X |
| Comparative Example 2-13 | Water Repellency 2C | moth-eye | 10 mm$^2$/s | 1000 rpm/12 sec | X | △ |
| Comparative Example 2-14 | Water Repellency 2C | moth-eye | 10 mm$^2$/s | Cloth Wiping | X | △ |
| Example 2-1 | Water Repellency 2 | moth-eye | 10 mm$^2$/s | 1000 rpm/12 sec | ◎ | ◎ |
| Example 2-2 | Water Repellency 2 | moth-eye | 10 mm$^2$/s | Pour-over | ○ | ◎ |
| Example 2-3 | Water Repellency 2 | moth-eye | 10 mm$^2$/s | 200 rpm/12 sec | ◎ | ◎ |
| Example 2-4 | Water Repellency 2 | moth-eye | 10 mm$^2$/s | 3500 rpm/12 sec | ◎ | ◎ |
| Example 2-5 | Water Repellency 2 | moth-eye | 350 mm$^2$/s | 1000 rpm/12 sec | △ | ○ |
| Example 2-6 | Water Repellency 2 | moth-eye | 350 mm$^2$/s | Pour-over | △ | ○ |
| Example 2-7 | Water Repellency 2 | moth-eye | 500 mm$^2$/s | 1000 rpm/12 sec | △ | ○ |
| Example 2-8 | Water Repellency 2 | moth-eye | 500 mm$^2$/s | Pour-over | △ | ○ |
| Example 2-9 | Water Repellency 2 | moth-eye | 10 mm$^2$/s | Cloth Wiping | ◎ | ◎ |
| Example 2-10 | Water Repellency 2A | moth-eye | 10 mm$^2$/s | 1000 rpm/12 sec | ◎ | ◎ |
| Example 2-11 | Water Repellency 2A | moth-eye | 10 mm$^2$/s | Cloth Wiping | ◎ | ◎ |
| Example 2-12 | Water Repellency 2B | moth-eye | 10 mm$^2$/s | 1000 rpm/12 sec | ○ | ○ |
| Example 2-13 | Water Repellency 2B | moth-eye | 10 mm$^2$/s | Cloth Wiping | ○ | ○ |
| Example 2-14 | Hydrophilicity 1Fc | moth-eye | 10 mm$^2$/s | 1000 rpm/12 sec | ○ | ○ |

TABLE 13

| | TEST 1 | TEST 2 | TEST 3 |
|---|---|---|---|
| Comparative Example 2-1 | Blood did not roll down. Flow mark remained. | It took time to thoroughly wash away. | Equivalent to TEST 1. |
| Comparative Example 2-2 | 2 drops adhered. Blood fall was somewhat slow. | Blood easily flowed but partially blurred. | Blood mixed with water, spread and blurred. |
| Comparative Example 2-3 | 1 drop adhered. | Blood easily flowed. | Blood mixed with water, spread and blurred. |
| Comparative Example 2-4 | Blood did not roll down. Flow mark remained. | Blood easily flowed. | Blood mixed with water, spread and blurred. |
| Comparative Example 2-5 | No blood adhered. Blood fall was somewhat slow. | Blood easily flowed. | Blood mixed with water, spread and blurred. |
| Comparative Example 2-6 | No blood adhered. Blood fall was somewhat slow. | Blood easily flowed. | Blood mixed with water, spread and blurred. |
| Comparative Example 2-7 | No blood adhered. Blood fall was somewhat slow. | Blood easily flowed. | Blood mixed with water, spread and blurred. |
| Comparative Example 2-8 | No blood adhered. Blood fall was somewhat slow. | Blood easily flowed. | Blood mixed with water, spread and blurred. |
| Comparative Example 2-9 | No blood adhered. Blood fall was somewhat slow. | Blood easily flowed. | Blood mixed with water, spread and blurred. |
| Comparative Example 2-10 | No blood adhered. Blood fall was somewhat slow. | Blood easily flowed. | Blood mixed with water, spread and blurred. |
| Comparative Example 2-11 | No blood adhered. Blood fall was somewhat slow. | Blood easily flowed. | Blood mixed with water, spread and blurred. |
| Comparative Example 2-12 | 1 drop adhered. Blood fall was slow. | Washer liquid remained in drops. | Blood mixed with water, spread and blurred. |
| Comparative Example 2-13 | 1 drop adhered. Blood fall was slow. | Washer liquid remained in drops. | Blood mixed with water, spread and blurred. |
| Comparative Example 2-14 | 1 drop adhered. Blood fall was slow. | Washer liquid remained in drops. | Blood mixed with water, spread and blurred. |

TABLE 14

| | TEST 1 | TEST 2 | TEST 3 |
|---|---|---|---|
| Example 2-1 | No blood adhered. | Washer liquid also cleanly flowed down. | Equivalent to TEST 1. |
| Example 2-2 | 2 drops adhered. Blood fall was somewhat slow. | Blood was easily washed away, but washer liquid blurred. | Equivalent to TEST 1. |
| Example 2-3 | No blood adhered. | Washer liquid also cleanly flowed down. | Equivalent to TEST 1. |
| Example 2-4 | No blood adhered. | Washer liquid also cleanly flowed down. | Equivalent to TEST 1. |
| Example 2-5 | 1 drop adhered. Blood fall was slow. | Washer liquid partially remained in drops. | Equivalent to TEST 1. |
| Example 2-6 | Blood fall was slow. | Washer liquid partially remained in drops. | Equivalent to TEST 1. |
| Example 2-7 | Blood fall was slow. | Washer liquid partially remained in drops. | Equivalent to TEST 1. |
| Example 2-8 | Blood fall was slow. | Washer liquid partially remained in drops. | Equivalent to TEST 1. |
| Example 2-9 | No blood adhered. | Washer liquid also cleanly flowed down. | Equivalent to TEST 1. |
| Example 2-10 | No blood adhered. | Washer liquid also cleanly flowed down. | Equivalent to TEST 1. |
| Example 2-11 | No blood adhered. | Washer liquid also cleanly flowed down. | Equivalent to TEST 1. |
| Example 2-12 | No blood adhered. Blood fall was somewhat slow. | Blood was easily washed away, but washer liquid blurred. | Equivalent to TEST 1. |
| Example 2-13 | No blood adhered. Blood fall was somewhat slow. | Blood was easily washed away, but washer liquid blurred. | Equivalent to TEST 1. |
| Example 2-14 | No blood adhered. Blood fall was somewhat slow. | Blood was easily washed away, but washer liquid blurred. | Equivalent to TEST 1. |

As seen from the foregoing results (particularly from the evaluation results of the effect durability shown in TABLE 12), only synthetic polymer films with the moth-eye structure at the surface which were produced using a water-repellent material (Example 2-1 to Example 2-13) and a synthetic polymer film with the moth-eye structure at the surface which was produced using a hydrophilic material and which had a water-repellent and oil-repellent layer of a sufficient thickness on the resin film (Example 2-14) are excellent in durability of the blood adhesion suppressing effect. That is, when a silicone oil is applied to a surface but the surface is hydrophilic, the blood adhesion suppressing effect would not last even though the surface has the moth-eye structure. This is probably because, during the washing, water enters between the surface of the synthetic polymer film and the silicone oil, and the silicone oil is washed away from the surface. It is estimated that the surface with the moth-eye structure which is made of a water-repellent material stably holds the silicone oil, and this effect of the water-repellent moth-eye surface is not marred by water used during the washing.

The water repellency of the surface of the synthetic polymer film with the silicone oil provided at the surface (for example, a surface of a resin film (water-repellent) which is made of a photocurable resin or a surface of a water-repellent and oil-repellent layer formed on a resin film which is made of a photocurable resin (the film may also be hydrophilic)) only requires that the static contact angle of water (at the lapse of 10 seconds since the landing of the drop) is not less than about 98° (more than 99°). This is supported by the results of Example 2-12 (Example 2B (Water Repellency 2B) in TABLE 5B).

As understood from the comparison between Example 2-14 and Comparative Example 2-12, the water-repellent moth-eye surface can also be realized by forming a water-repellent and oil-repellent layer of a sufficient thickness on the moth-eye surface of a synthetic polymer film which is made of a hydrophilic material. Preferably, the thickness of the water-repellent and oil-repellent layer is, for example, not less than 5 nm. The static contact angle of water (at the lapse of 10 seconds since the landing of the drop) is preferably not less than 103° (see TABLE 11).

Comparing Example 2-1 to Example 2-14, it can be said that the silicone oil preferably has a lower kinematic viscosity. Example 2-1 to Example 2-4 and Example 2-9 to Example 2-14 in which the kinematic viscosity of the silicone oil used was 10 mm$^2$/s exhibited better durability in the blood adhesion suppressing effect than Example 2-5 to Example 2-8 in which the kinematic viscosity of the silicone oil used was equal to or higher than 350 mm$^2$/s. Therefore, it can be said that a silicone oil which has at least a kinematic viscosity of lower than 350 mm$^2$/s is preferred, and a silicone oil which has at least a kinematic viscosity equal to or lower than 10 mm$^2$/s is more preferred. This is probably because the structure shown in FIG. 7(a) is more likely to be realized as the kinematic viscosity decreases, and the structure shown in FIG. 7(b) is more likely to be realized as the kinematic viscosity increases. That is, it is estimated that the effect of improving the water and oil repellency which is achieved by the moth-eye structure contributes to the structure shown in FIG. 7(a). As for the method of applying the silicone oil to the surface, no difference was found among Method 1 to Method 3, and any of the methods which is convenient in clinical workplaces or the like can be employed.

Next, the evaluation results of the antifog property of the sample films are described. When an endoscope is inserted into a body, dew condensation forms sometimes. This is because both temperature and humidity are higher inside the body than an operating room that is usually regulated to a relatively low temperature. As a matter of course, preferably, the endoscope distal end cover can suppress this type of dew condensation.

As the sample films, the above-described sample films (Example 2-1, Comparative Example 2-11, Comparative Example 2-4, Comparative Example 2-5) were used.

According to the test method employed herein, the respective sample films were left in a pre-test environment at a low temperature and a low humidity for one hour or longer so as to be sufficiently acclimated to the environment. Thereafter, within 10 seconds, each of the sample films was put into a test environment at a high temperature and a high humidity, and the state of dew condensation at the surface of the sample film (antifog property) was observed with an eye. The results are shown in TABLE 15. In TABLE 15, ⊚: not fogged, Δ: slightly fogged, x: fogged (water drops formed), xx: wet (water drops formed over the entire surface).

TABLE 15

| | | Pre-test Environment | | | |
|---|---|---|---|---|---|
| | | 5° C./10% RH | | 5° C./10% RH | |
| | | Test Environment | | | |
| | | 30° C./85% RH | | 25° C./50% RH | |
| | Silicone Oil | Provided | Not provided | Provided | Not provided |
| Material | PET | X | X | X | X |
| | Water | ○ | Δ | ○ | ○ |
| | Repellency 2 | Example 2-1 | Comparative Example 2-11 | Example 2-1 | Comparative Example 2-11 |
| | Hydrophilicity 1 | XX Comparative Example 2-5 | XX Comparative Example 2-4 | ○ Comparative Example 2-5 | ○ Comparative Example 2-4 |

In a test environment at 25° C./50% RH, the presence/absence of silicone resulted in no difference between the hydrophilic moth-eye and the water-repellent moth-eye. In a test environment at 30° C./85% RH which is closer to the environment inside the body, formation of dew condensation occurred at the surface of the sample film with the hydrophilic moth-eye so that the entire surface was wet, while no fog occurred in an example where the surface of the water-repellent moth-eye was provided with the silicone oil. When the silicone oil was not applied to the surface of the water-repellent moth-eye, the surface was slightly fogged. It is thus concluded that the effect of preventing dew condensation was improved by applying the silicone oil to the water-repellent moth-eye surface. As seen from this result, from the viewpoint of antifog property, it is preferred to use the water-repellent moth-eye. It is estimated that the difference in the above-described results between the water-repellent moth-eye and the hydrophilic moth-eye with the silicone oil applied to the surface is attributed to the state where the moth-eye structure is not thoroughly filled with the silicone oil (the state shown in FIG. 7(a)).

INDUSTRIAL APPLICABILITY

An endoscope distal end cover and an endoscope of an embodiment of the present invention are capable of suppressing adhesion of blood or body fluid to an observation window and easily securing the visual field for observation.

REFERENCE SIGNS LIST

10, 10A-10G: endoscope distal end cover
12, 12A, 12B: base film
13, 13A, 13B: synthetic polymer film
13Ap, 13Bp: raised portion
14, 14A, 14B, 14Asa, 14Asb, 14Asc: film
15, 15a, 15b: adhesive layer
16: cover member
17: adhesive layer
19: air layer
18: securing member
20t: distal end
20, 20A, 20B, 20C: endoscope
20a: insertion section
20b: control section
22: attachment
32: observation window
34a, 34b: illumination window
36: forceps opening
38: ejection nozzle
42: trocar
44: valve
54: liquid supply tube
62A, 62B: water-repellent oil
100: endoscope system

The invention claimed is:

1. An endoscope distal end cover for protecting a distal end of an endoscope which has an observation window at the distal end, comprising:
   a synthetic polymer film which is to be located over the observation window when the endoscope distal end cover is attached to the distal end of the endoscope,
   wherein the synthetic polymer film has a surface which includes a plurality of raised portions,
   when viewed in a normal direction of the synthetic polymer film, a two-dimensional size of the plurality of raised portions is in the range of more than 20 nm and less than 500 nm,
   a static contact angle of water with respect to the surface is not less than 98°,
   the synthetic polymer film includes a resin film which is made of a photocurable resin,
   the photocurable resin contains a first polymerizable fluoric compound which contains a fluorine element,
   the first polymerizable fluoric compound has a plurality of polymerizable functional groups and has a molecular weight of not less than 1000 and not more than 5000, and
   at the lapse of 5 minutes since placing a 200 μL drop of water on the surface of the synthetic polymer film, a pH of an aqueous solution is not less than 6.5 and not more than 7.5.

2. The endoscope distal end cover of claim 1, wherein the static contact angle of water with respect to the surface of the synthetic polymer film is not less than 128°.

3. The endoscope distal end cover of claim 1, further comprising a liquid film of a water-repellent oil covering a surface of at least a portion of the synthetic polymer film located on the observation window.

4. The endoscope distal end cover of claim 3, wherein the water-repellent oil is a silicone oil or a fluoric oil.

5. The endoscope distal end cover of claim 3, wherein the water-repellent oil is a silicone oil whose kinematic viscosity is lower than 350 mm$^2$/s.

6. The endoscope distal end cover of claim 3, wherein the water-repellent oil is a silicone oil whose kinematic viscosity is equal to or lower than 10 mm$^2$/s.

7. The endoscope distal end cover of claim 1, wherein the synthetic polymer film further includes a water-repellent and oil-repellent layer formed on the resin film.

8. The endoscope distal end cover of claim 1, wherein
the photocurable resin contains a photopolymerization initiator, and
the photopolymerization initiator contains at least one of the group consisting of ethanone, 1-[9-ethyl-6-(2-methylbenzoyl)-9H-carbazole-3-yl]-, 1-(O-acetyloxime), 2-hydroxy-1-{4-[4-(2-hydroxy-2-methyl-propionyl)-benzyl]phenyl}-2-methyl-propan-1-one, and 1-[4-(2-hydroxyethoxy)-phenyl]-2-hydroxy-2-methyl-1-propane-1-one.

9. The endoscope distal end cover of claim 1, wherein
the photocurable resin further contains a second polymerizable fluoric compound which contains the fluorine element, and
the second polymerizable fluoric compound is a monofunctional polymerizable compound and has a molecular weight of not less than 100 and not more than 1000.

10. The endoscope distal end cover of claim 1, wherein a proportion of the first polymerizable fluoric compound to the photocurable resin is not less than 1 mass % and not more than 5 mass %.

11. An endoscope comprising the endoscope distal end cover as set forth in claim 1, the endoscope distal end cover being attached to the endoscope.

12. The endoscope distal end cover of claim 1, further comprising a liquid film of a water-repellent oil covering a surface of at least a portion of the synthetic polymer film located on the observation window, wherein
the synthetic polymer film further includes a water-repellent and oil-repellent layer formed on the resin film.

* * * * *